United States Patent
Mahoney et al.

(10) Patent No.: US 9,180,024 B2
(45) Date of Patent: Nov. 10, 2015

(54) SYSTEMS AND METHODS FOR SPINAL SURGERY

(75) Inventors: Michael Mahoney, Middletown, RI (US); Sara Dziedzic, Dorchester, MA (US); Paul Birkmeyer, Marshfield, MA (US); Timothy Beardsley, Kingston, MA (US); Dale Frank, Taunton, MA (US); Ron Naughton, Westfield, NJ (US)

(73) Assignee: Medos International Sarl, Le Locle (CH)

( * ) Notice: Subject to any disclaimer, the term of this patent is extended or adjusted under 35 U.S.C. 154(b) by 853 days.

(21) Appl. No.: 13/185,775

(22) Filed: Jul. 19, 2011

(65) Prior Publication Data

US 2011/0276139 A1     Nov. 10, 2011

Related U.S. Application Data

(62) Division of application No. 10/579,146, filed as application No. PCT/US2005/004136 on Feb. 9, 2005, now Pat. No. 8,016,829.

(60) Provisional application No. 60/543,030, filed on Feb. 9, 2004.

(51) Int. Cl.
*A61B 17/56* (2006.01)
*A61F 2/46* (2006.01)
(Continued)

(52) U.S. Cl.
CPC ............. *A61F 2/4611* (2013.01); *A61B 17/025* (2013.01); *A61F 2/447* (2013.01);
(Continued)

(58) Field of Classification Search
CPC ...................................... A61F 2/4611

USPC .......................... 606/86 A, 86 B, 99
See application file for complete search history.

(56) References Cited

U.S. PATENT DOCUMENTS

| 4,743,256 A | 5/1988 | Brantigan |
| 4,834,757 A | 5/1989 | Brantigan |

(Continued)

FOREIGN PATENT DOCUMENTS

| EP | 126642 A2 | 11/1984 |
| EP | 0860152 B1 | 8/1998 |

(Continued)

OTHER PUBLICATIONS

Brantigan, J. et al., "Posterior Lumbar Interbody Fusion Technique Using the Variable Screw Placement Spinal Fixation System," Spine: State of the Art Reviews, 6(1):175-200 (Jan. 1992).

(Continued)

*Primary Examiner* — Nicholas Woodall
(74) *Attorney, Agent, or Firm* — Nutter McClennen & Fish LLP

(57) ABSTRACT

Disclosed herein are methods and devices for distracting adjacent vertebrae during surgical procedures for implanting spinal prostheses. In an exemplary embodiment, a distractor is disclosed that maintains the empty space between adjacent vertebrae following a discectomy, and that can removably mate with other surgical instruments, such as, for example, a filler bar, an implanting tool, or a funnel. In other embodiments of the present invention a distractor is disclosed having various features to assist in implanting a spinal prosthesis, such as, for example, an angled distal end and/or an expandable paddle. In another embodiment of the present invention, an articulating inserter is disclosed. Moreover, various implants and funnels are also disclosed herein.

9 Claims, 25 Drawing Sheets

(51) Int. Cl.
*A61B 17/02* (2006.01)
*A61F 2/44* (2006.01)
*A61F 2/28* (2006.01)
*A61F 2/30* (2006.01)

(52) U.S. Cl.
CPC ...... *A61F 2/4601* (2013.01); *A61B 2017/0256* (2013.01); *A61F 2/28* (2013.01); *A61F 2/30965* (2013.01); *A61F 2002/3038* (2013.01); *A61F 2002/3052* (2013.01); *A61F 2002/30062* (2013.01); *A61F 2002/30092* (2013.01); *A61F 2002/30112* (2013.01); *A61F 2002/30133* (2013.01); *A61F 2002/30217* (2013.01); *A61F 2002/30235* (2013.01); *A61F 2002/30266* (2013.01); *A61F 2002/30462* (2013.01); *A61F 2002/30471* (2013.01); *A61F 2002/30476* (2013.01); *A61F 2002/30538* (2013.01); *A61F 2002/30566* (2013.01); *A61F 2002/30772* (2013.01); *A61F 2002/30795* (2013.01); *A61F 2002/30841* (2013.01); *A61F 2002/30904* (2013.01); *A61F 2002/4415* (2013.01); *A61F 2002/4622* (2013.01); *A61F 2002/4627* (2013.01); *A61F 2002/4628* (2013.01); *A61F 2210/0004* (2013.01); *A61F 2210/0014* (2013.01); *A61F 2220/0025* (2013.01); *A61F 2220/0033* (2013.01); *A61F 2220/0075* (2013.01); *A61F 2220/0091* (2013.01); *A61F 2230/0004* (2013.01); *A61F 2230/0015* (2013.01); *A61F 2230/0067* (2013.01); *A61F 2230/0069* (2013.01); *A61F 2230/0082* (2013.01); *A61F 2250/0006* (2013.01); *A61F 2310/00017* (2013.01); *A61F 2310/00023* (2013.01); *A61F 2310/00029* (2013.01); *A61F 2310/00131* (2013.01); *A61F 2310/00359* (2013.01)

(56) References Cited

U.S. PATENT DOCUMENTS

| | | | |
|---|---|---|---|
| 4,878,915 | A | 11/1989 | Brantigan |
| 5,192,327 | A | 3/1993 | Brantigan |
| 5,425,772 | A | 6/1995 | Brantigan |
| 5,443,514 | A | 8/1995 | Steffee |
| 5,609,635 | A | 3/1997 | Michelson |
| 5,658,336 | A | 8/1997 | Pisharodi |
| 5,716,415 | A | 2/1998 | Steffee |
| 5,766,252 | A | 6/1998 | Henry et al. |
| 5,957,927 | A | 9/1999 | Magee et al. |
| 5,984,922 | A | 11/1999 | McKay |
| 6,059,790 | A | 5/2000 | Sand et al. |
| 6,059,829 | A | 5/2000 | Schlapfer |
| 6,080,158 | A | 6/2000 | Lin |
| 6,086,593 | A | 7/2000 | Bonutti |
| 6,086,595 | A | 7/2000 | Yonemura et al. |
| 6,099,531 | A | 8/2000 | Bonutti |
| 6,156,040 | A | 12/2000 | Yonemura et al. |
| 6,174,311 | B1 | 1/2001 | Branch et al. |
| 6,224,599 | B1 | 5/2001 | Bayham |
| 6,245,108 | B1 | 6/2001 | Biscup |
| 6,270,498 | B1 | 8/2001 | Michelson |
| 6,277,149 | B1 | 8/2001 | Boyle |
| 6,368,325 | B1 | 4/2002 | McKinley |
| 6,432,140 | B1 | 8/2002 | Lin |
| 6,443,987 | B1 | 9/2002 | Bryan |
| 6,478,800 | B1 | 11/2002 | Fraser et al. |
| 6,485,517 | B1 | 11/2002 | Michelson |
| 6,500,205 | B1 | 12/2002 | Michelson |
| 6,500,206 | B1 | 12/2002 | Bryan |
| 6,530,955 | B2 | 3/2003 | Boyle et al. |
| 6,533,752 | B1 | 3/2003 | Waram et al. |
| 6,537,320 | B1 | 3/2003 | Michelson |
| 6,569,168 | B2 | 5/2003 | Lin |
| 6,582,437 | B2 | 6/2003 | Dorchak et al. |
| 6,595,995 | B2 | 7/2003 | Zdeblick et al. |
| 6,595,998 | B2 | 7/2003 | Johnson et al. |
| 6,599,291 | B1 | 7/2003 | Foley et al. |
| 6,599,294 | B2 | 7/2003 | Fuss |
| 6,610,089 | B1 | 8/2003 | Liu et al. |
| 6,613,091 | B1 | 9/2003 | Zdeblick et al. |
| 6,620,126 | B2 | 9/2003 | Unsworth et al. |
| 6,626,913 | B1 | 9/2003 | McKinnon et al. |
| 6,635,086 | B2 | 10/2003 | Lin |
| 6,645,206 | B1 | 11/2003 | Zdeblick et al. |
| 6,648,895 | B2 | 11/2003 | Burkus et al. |
| 6,666,866 | B2 | 12/2003 | Martz et al. |
| 6,830,570 | B1 | 12/2004 | Frey et al. |
| 6,991,654 | B2 | 1/2006 | Foley et al. |
| 7,235,082 | B2 * | 6/2007 | Bartish et al. .................. 606/99 |
| 7,575,580 | B2 * | 8/2009 | Lim et al. ........................ 606/99 |
| 7,618,423 | B1 | 11/2009 | Valentine et al. |
| 8,016,829 | B2 | 9/2011 | Mahoney et al. |
| 8,114,092 | B2 * | 2/2012 | Altarac et al. .................. 606/99 |
| 8,118,872 | B2 * | 2/2012 | Trudeau et al. ............ 623/17.16 |
| 8,425,529 | B2 * | 4/2013 | Milz et al. ....................... 606/99 |
| 8,491,598 | B2 * | 7/2013 | Crook ............................. 606/99 |
| 2001/0031968 | A1 | 10/2001 | Dorchak et al. |
| 2002/0010473 | A1 | 1/2002 | Lin |
| 2002/0016592 | A1 | 2/2002 | Branch et al. |
| 2002/0026242 | A1 | 2/2002 | Boyle et al. |
| 2002/0045904 | A1 | 4/2002 | Fuss et al. |
| 2002/0077632 | A1 | 6/2002 | Tsou |
| 2002/0165550 | A1 | 11/2002 | Frey et al. |
| 2002/0188295 | A1 | 12/2002 | Martz et al. |
| 2002/0198532 | A1 | 12/2002 | Michelson |
| 2003/0023306 | A1 | 1/2003 | Lin et al. |
| 2003/0032966 | A1 | 2/2003 | Foley |
| 2003/0083748 | A1 | 5/2003 | Lee et al. |
| 2003/0105527 | A1 | 6/2003 | Bresina |
| 2003/0114931 | A1 | 6/2003 | Lee |
| 2003/0130667 | A1 | 7/2003 | Lin |
| 2003/0135275 | A1 | 7/2003 | Garcia et al. |
| 2003/0139812 | A1 | 7/2003 | Garcia et al. |
| 2003/0139814 | A1 | 7/2003 | Bryan |
| 2003/0149438 | A1 | 8/2003 | Nichols et al. |
| 2003/0195626 | A1 | 10/2003 | Huppert |
| 2003/0208203 | A1 | 11/2003 | Lim et al. |
| 2004/0015168 | A1 | 1/2004 | Yonemura |
| 2004/0117019 | A1 | 6/2004 | Trieu et al. |
| 2004/0117020 | A1 | 6/2004 | Frey et al. |
| 2004/0153065 | A1 | 8/2004 | Lim |
| 2005/0027360 | A1 | 2/2005 | Webb et al. |
| 2005/0131420 | A1 | 6/2005 | Techiera et al. |
| 2007/0276406 | A1 | 11/2007 | Mahoney et al. |
| 2009/0054991 | A1 * | 2/2009 | Biyani et al. ................ 623/17.16 |

FOREIGN PATENT DOCUMENTS

| | | |
|---|---|---|
| WO | WO 0033752 | 6/2000 |
| WO | WO 0128466 | 4/2001 |
| WO | WO 0217823 | 3/2002 |
| WO | WO 0238086 | 5/2002 |

OTHER PUBLICATIONS

European Search Report, from corresponding EP Appl. No. 05713229.2, mailed Jan. 16, 2009.
International Search Report, from corresponding PCT/US05/04136, mailed Jul. 25, 2005.

* cited by examiner

SYSTEMS AND METHODS FOR SPINAL SURGERY

RELATED APPLICATIONS

The present application is a divisional of U.S. application Ser. No. 10/579,146, filed Feb. 22, 2007, which is a U.S. national phase application filed pursuant to 35 U.S.C. 371 from PCT/US05/004136, filed Feb. 9, 2005, which claims the benefit of the filing date of U.S. Provisional Patent Application Ser. No. 60/543,030, filed Feb. 9, 2004, all of which are herein incorporated by reference.

FIELD OF THE INVENTION

The present invention relates to surgical instruments, and in particular to methods and devices for implanting spinal prostheses.

BACKGROUND

Spinal fusion surgeries, that is, the use of bone graft material to promote specific vertebrae to grow together into a solid and stable construct, are a common method of treating patients with severe back pain. For fusion to occur within the disc space, the surgeon must first remove the damaged disk material. Once the disk material is removed, the empty space left between the upper and lower vertebrae is distracted to relieve pressure from neural elements and to provide space for entry of surgical tools and/or implants. A bone graft, or interbody cage with bone, is then inserted into the empty disc space to promote bone growth from vertebral body to vertebral body. Recently, minimally invasive techniques have improved fusion procedures by causing less damage to tissue surrounding the damaged disk and allowing for faster recovery by the patient.

One drawback associated with current instruments used to perform spinal fusion surgery, especially minimally invasive surgery, is that they typically provide inadequate protection for sensitive nerve tissue surrounding the surgical site. The smaller access portals used in minimally invasive surgery allow sensitive tissue to be located very close to the surgical site. Further, using current instruments within these tight confines often impedes the surgeon's visibility, making the ultimate placement of the implant difficult.

Accordingly, there remains a need for improved surgical instruments, and in particular for surgical instruments used for implanting spinal prostheses.

SUMMARY

Disclosed herein are various methods and devices for implanting spinal prostheses. In one aspect, a surgical instrument system includes a distractor having a shaft, a paddle located at the distal end of the shaft, and a filler bar shaped to removably engage the shaft and paddle of the distractor. In an exemplary embodiment, when the filler bar is engaged to the distractor, the filler bar provides rigidity and torque strength so that the distractor can be inserted between adjacent vertebrae in a first orientation and rotated to distract adjacent vertebrae. A guide feature configured to mate with at least one of an implant or an implant inserter can extend along at least a portion of the shaft and the paddle, or alternatively, the paddle can further comprise at least one overhanging tab on at least one of the superior and inferior surfaces. Moreover, in a further exemplary embodiment, the surgical instrument system can comprise a minimally invasive access port through which is distractor is dimensioned to be placed.

In a further embodiment, at least one of the superior and inferior surfaces of the paddle can include a means for preventing migration of the distractor during distraction, such as, for example a bone engaging element or at least one expansion shoulder. The distractor paddle can also include an angled guide feature that is configured to guide an implant through a partial rotation to a desired angle. The angled guide feature can have a variety of configurations, such as an angled surface integral with a distal portion of the paddle, or, a movable shim that can be either retractable or a memory metal shim. The implant inserter can also include an angled distal end or an articulating implant holder operable to rotate an implant to a desired angle.

In a further aspect, a surgical instrument system includes a distractor having a shaft and a paddle located on the distal end of the shaft. The distractor paddle and the shaft can also present a guide surface for guiding the placement of an implant when the distractor is in the distraction orientation. The distractor paddle can also include an angled guide feature that is configured to guide an implant through a partial rotation to a desired angle. The angled guide features can have a variety of configurations, such as an angled surface integral with a distal portion of the paddle, or, a movable shim that can be either retractable or a memory metal shim. The distractor paddle can also include a first height dimension when presented in an insertion orientation and a second height dimension when rotated approximately 90 degrees to a distraction orientation, the second height dimension being greater than the first height dimension, the paddle having inferior and superior surfaces for contacting adjacent vertebrae in the distraction orientation. In a further embodiment, at least one of the superior and inferior surfaces of the paddle can include a means for preventing migration of the distractor during distraction, such as, for example a bone engaging element including at least one tooth or at least one expansion shoulder operable to extend beyond at least one of the inferior or superior surfaces so as to increase the second height dimension.

In a further embodiment, the surgical instrument system can also include an implant inserter having an angled distal end, the angle corresponding approximately to the angle provided on the angled guide feature or having an articulating implant holder operable to rotate an implant to a desired angle. Moreover, the surgical instrument system can also include guide features extending along the shaft and paddle configured for mating with at least one of an implant and an implant inserter to guide the insertion of an implant along the distractor. In a further embodiment, the surgical instrument system can include a filler bar shaped to removably engage the shaft and paddle of the distractor, wherein when the filler bar is engaged to the distractor, the filler bar provides rigidity and torque strength so that the distractor can be inserted between adjacent vertebrae in a first orientation and rotated to distract the adjacent vertebrae. The surgical instrument system can also include a minimally invasive access port through which the distractor is dimensioned to be placed.

In another aspect, a surgical instrument system includes a distractor having a shaft and a paddle located on the distal end of the shaft, the paddle further including inferior and superior surfaces configured for contacting adjacent vertebrae to define a distraction height. The surgical instrument system also includes at least one expansion shoulder operable to extend beyond at least one of the inferior or superior surfaces of the paddle so as to increase the distraction height. In one embodiment, the surgical instrument system can include a shim that can be slidable along a longitudinal axis of the distractor, and that can further include at least one expansion shoulder such that the distal movement of the shim causes the at least one expansion shoulder to increase the distraction height. The shim can also include an angled distal end such that distal movement of the shim causes the angled distal end to extend at an angle from a distal end of the paddle to form an angled guide. The system can further include a linkage assembly slidably connecting the paddle and the at least one extension shoulder, or, alternatively, a slidable shim having a shoulder for contacting the linkage assembly to effect changes in the distraction height. Moreover, the distractor paddle and the shaft can present a guide surface, which can optionally include a guide feature, for guiding the placement of an implant when the distractor in the distraction orientation.

In still another aspect, the surgical instrument system can include an articulating implant inserter including a shaft, and an articulatable implant holding element located at the distal end of the shaft. The articulatable implant holding element can be operable from the proximal portion of the shaft to releasably hold an implant. Moreover, the surgical system can further include an implant having a connecting element that cooperates with the articulatable implant holding element to allow articulation of the implant to a desired angle. The implant connecting element can engage either an internal or external portion of the implant. Further, the articulatable implant holding element can include two sliding elements having distal implant impaction faces, such that the relative sliding of the sliding elements in a proximal-distal direction along the shaft selectively articulates the implant to a desired angle. The position of the handle can also act as a visual indicator for an angle through which the implant has been rotated.

In still another aspect, a surgical instrument system disclosed herein includes a means for distracting adjacent vertebrae, an implant, a means for inserting the implant into a space between the adjacent vertebrae upon insertion, and a means for rotating the implant to a desired angle between the adjacent vertebrae upon insertion. In certain embodiments, the means for distracting adjacent vertebrae includes two distraction paddles movable away from each other to distract adjacent vertebrae, or a distractor paddle having a first height dimension when presented in an insertion orientation and a second height dimension when rotated approximately 90 degrees to a distraction orientation, the second height dimension being greater than the first height dimension.

Moreover, the surgical instrument system can also include a shaft, a paddle located on the distal end of the shaft having inferior and superior surfaces configured for contacting adjacent vertebrae to define a distraction height, and at least one expansion shoulder operable to extend beyond at least one of the inferior or superior surfaces so as to increase the distraction height. While the means for insertion can vary, it can include a ratchet gun, or an articulating implant inserter operable to place the implant at a desired angle. The means for rotating the inserter can also vary can, and can include an articulating implant inserter or angled guide features located on a distal end of the means for distracting. Moreover, the implant can have a variety of configurations such as domed inferior and superior surfaces configured to correspond to surfaces of adjacent vertebra, or alternatively, a leading end having a bullet-shaped cross-sectional profile in at least two planes.

A method is provided in another aspect. In particular, a minimally invasive surgical method includes inserting a distractor assembly through a minimally invasive surgical access port and between adjacent vertebrae in an insertion orientation, the distractor assembly including a shaft, and a paddle located on the distal end of the shaft and a filler bar removably engaged to the shaft and the paddle of the distractor. The method can further include rotating the distractor assembly to a distraction orientation to distract the adjacent vertebrae, disengaging the filler bar from the shaft and paddle, and removing the filler bar through the minimally invasive access port while leaving the shaft and paddle in place to maintain a desired distraction of the adjacent vertebrae. In one embodiment, the distractor paddle includes a first height dimension when presented in an insertion orientation and a second height dimension when rotated approximately 90 degrees to a distraction orientation, the second height dimension being greater than the first height dimension. The paddle further includes inferior and superior surfaces for contacting adjacent vertebrae in the distraction orientation.

Moreover, the method can also include inserting an implant between the adjacent vertebrae using the shaft and paddle as a guide for placement of the implant. Alternatively, the method can include using a paddle with an angled guide element on its distal end, inserting the implant using the shaft and paddle as a guide for placement, and rotating the implant to a desired angle based on the angled guide element.

In a further aspect, an implant is provided. In one embodiment, the implant has a blended or "bullet-shaped" cross-sectional profile in at least two planes. In a further embodiment, the implant has a domed superior and/or inferior configured to conform generally to one or both adjacent vertebral end-plates at a predetermined angle of orientation of the implant. The implant can be combined with either a distractor that can guide the implant to the desired orientation (including a partial rotation of the implant) or an articulating insertion tool that can rotate the implant to the desired position.

BRIEF DESCRIPTION OF THE DRAWINGS

The invention will be more fully understood from the following detailed description taken in conjunction with the accompanying drawings, in which.

DETAILED DESCRIPTION OF THE EXEMPLARY EMBODIMENTS

Disclosed herein are methods and devices for distracting adjacent vertebrae and/or inserting spinal implants during surgical procedures for repairing a patient's spine. In an exemplary embodiment, a distractor is disclosed that maintains the empty space between adjacent vertebrae following a discectomy, and that can removably mate with other surgical instruments, such as, for example, a filler bar, an implanting tool, or a funnel. In other embodiments of the present invention a distractor is disclosed having various features to assist in implanting a spinal prosthesis, such as, for example, an angled distal end and/or an expandable paddle. In another embodiment of the present invention, an articulating inserter is disclosed. Moreover, various implants and funnels are also disclosed herein. A person skilled in the art will appreciate that, while the methods and devices are described in connection with certain spinal procedures, the methods and devices disclosed herein can be used for a variety of surgical procedures.

Certain features and aspects of the present invention will now be described by reference to the distractor assembly and associated elements illustrated in FIGS. 1 to 8, which illustrate a distractor assembly system and method for inserting a spinal prosthesis.

Figure 1:
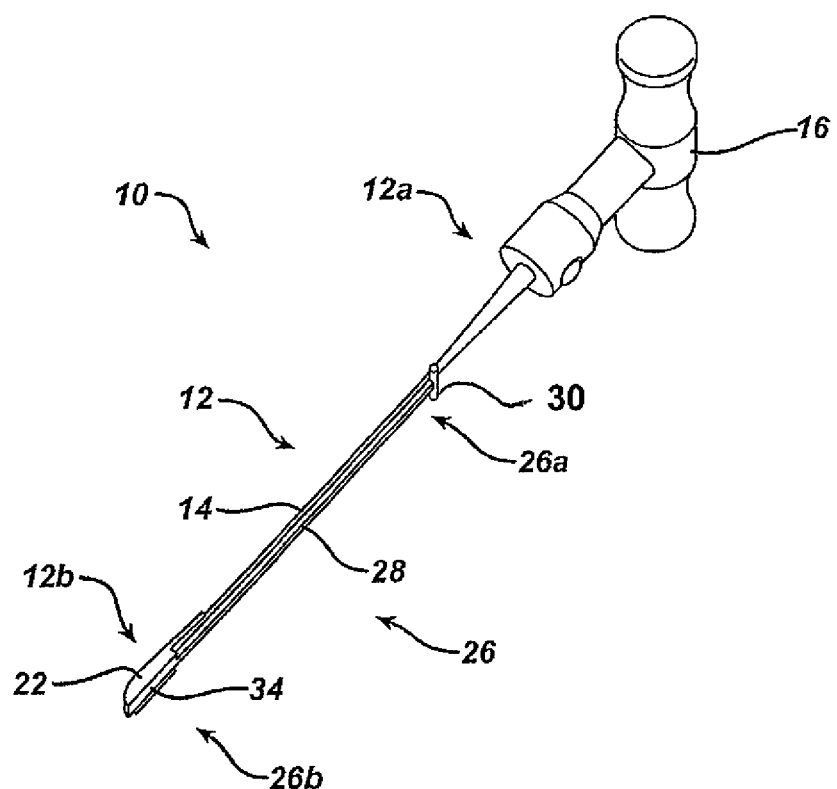
FIG. 1 is a side perspective view of one embodiment of a distractor assembly.
Figure 2:
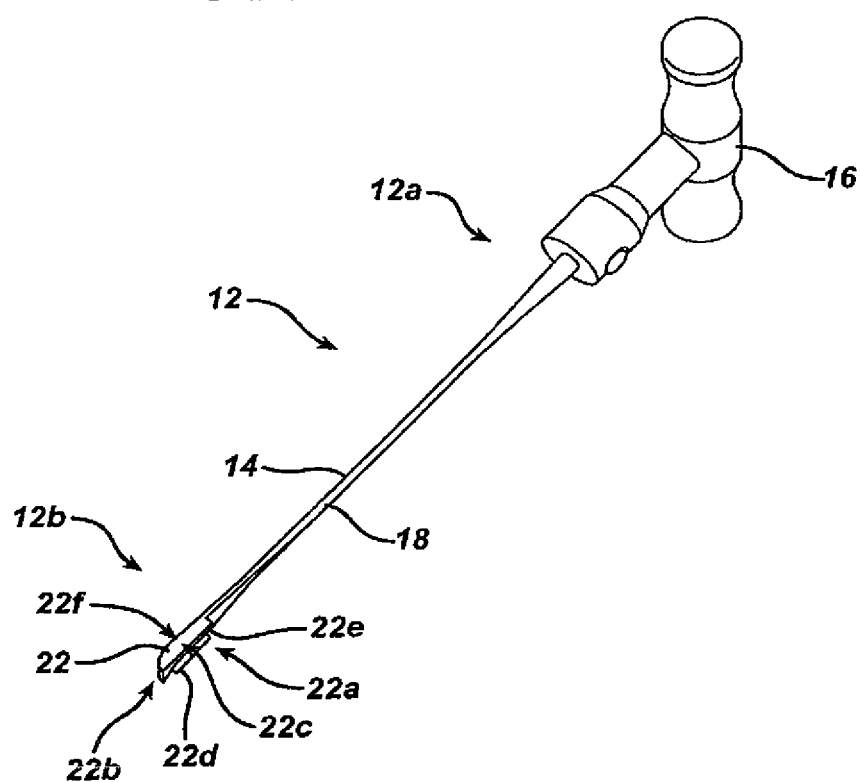
FIG. 2 is a side perspective view of one embodiment of the distractor of the distractor assembly of FIG. 1.
Figure 3:
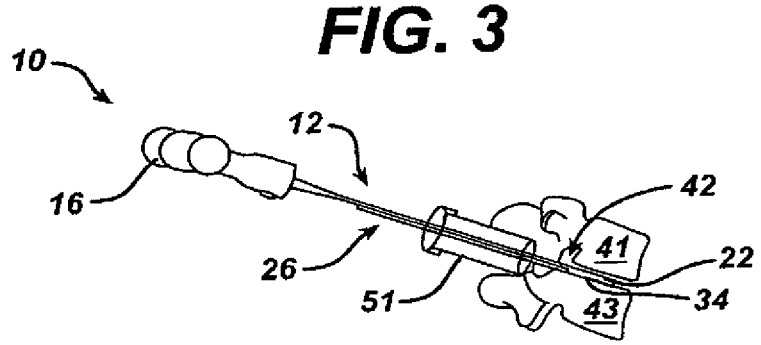
FIG. 3 is a side perspective view of the distractor assembly of FIG. 1 upon insertion into an intervertebral space.
Figure 4:
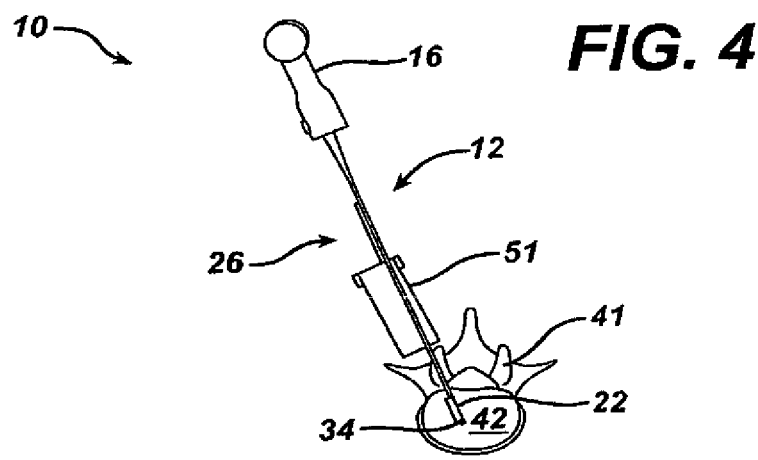
FIG. 4 is a top perspective view of the distractor assembly of FIG. 1 upon insertion into an intervertebral space.
Figure 5:
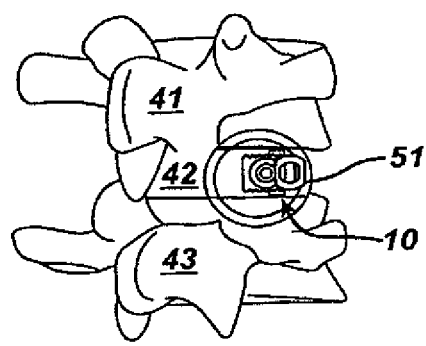
FIG. 5 is side perspective view of the distractor assembly of FIG. 1 upon insertion into an intervertebral space.
Figure 6:
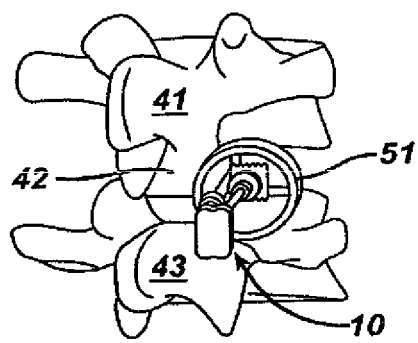
FIG. 6 is another side perspective view of the distractor assembly of FIG. 1 upon insertion into an intervertebral space.

FIG. 1 illustrates one embodiment of a distractor assembly 10 disclosed herein having a distractor or guide arm 12, a guide filler bar 26, and a modular handle 16. While the distractor 12 can have a variety of configurations that enable it to maintain the space between adjacent vertebrae following a discectomy, as shown in FIG. 2, the distractor 12 has proximal and distal ends 12a, 12b with an elongate shaft 14 extending therebetween. Attached to the proximal end 12a of the distractor 12 is a handle 16 (or a portion thereof) for gripping by the surgeon. While the handle 16 can be either fixedly or removably attached, in an exemplary embodiment, the handle 16 is removably attached to the shaft 14 by any means known in the art, such as, for example, a screw or a spring plunger, so that the surgeon can remove it to achieve increased visibility to the surgical site.

Extending distally from the handle 16 is an elongate shaft 14. While the shaft 14 can have a variety of sizes, it should have a diameter that, upon insertion into the intervertebral space, allows sufficient space for the insertion of other surgical tools, such as a filler bar or an inserter for example, as well as an implant. Additionally, the shaft 14 can have a variety of shapes, such as circular, ovular, rectangular or square. As shown, the shaft 14 is rectangular and generally flat.

The shaft 14 can also have a variety of configurations that allow for mating with another surgical instrument, such as, for example, a filler bar, an inserter, a funnel, or any other instrument used in the implanting of a spinal prosthesis. In an exemplary embodiment, the shaft 14 can have a guide feature 18 such as a tooth or groove that can mate with a corresponding guide feature on another surgical instrument. The guide feature 18 can be formed either throughout the entire length of the shaft 14 or on a partial length thereof. The guide feature 18 can also have a variety of configurations depending upon the mating features of the corresponding surgical instrument. For example, in one embodiment, the guide feature 18 can be protrude from the shaft 12, or, alternatively, the guide feature 18 can be recessed within the shaft 12. The guide feature 18 can also have a variety of shapes, however in an exemplary embodiment, the guide feature 18 has a C-shape with two opposed sides that are either straight or curved. In addition, outer features, including the cross-sectional shape of the shaft itself, can form mating or guiding features.

Attached to the distal-most end of the shaft 14 is a distracting paddle 22 that, upon insertion into the cavity, can be rotated to distract adjacent vertebrae to maintain the integrity of the cavity between them. As shown, paddle 22 has proximal and distal ends 22a, 22b connected by superior and inferior sides 22c, 22d and having a front or guiding face 22e and a back face 22f. While paddle 22 can have a variety of shapes, such as rectangular, circular or oblong, the illustrated paddle 22 is generally rectangular with rounded corners. The paddle 22 can also have a variety of sizes to provide a desired level of distraction, so long as it has a width that is less than the diameter of any access portal into the intervertebral space. In an exemplary embodiment, the paddle 22 has a width that is less than about 19 mm, and more preferably about 7 mm. The paddle may also be shaped so as to provide an angle between the inferior and superior sides to match a desired angle of distraction.

The paddle 22 can have a variety of additional features to assist the surgeon with distraction, which can be used alone or in combination with one another. In addition to those features discussed in more detail below, in one embodiment, the distal end 22b of the paddle 22 can be arcuate to allow for easier insertion into the intervertebral space 42. In addition, the superior and/or inferior sides 22c, 22d can have various geometries to enhance the distraction of the intervertebral space 42, such as laterally extending surfaces that provide a larger surface area to contact the vertebrae. The back side 22f can also be dome-shaped to aid the surgeon in minimizing damage to the neural tissue surrounding the intervertebral space 42. One of superior and inferior sides 22c, 22d can also be provided with a bone engaging element such as one or more teeth to prevent migration of the paddle during distraction.

Additionally the paddle 22 can have a variety of features to assist the surgeon with positioning of the implant 48 within the intervertebral space 42. In addition to those features discussed in more detail below, guide surface 22e of the paddle 22 can include at least one guide feature such as guide feature 18 extending from the shaft 14 to engage a corresponding element in an implant or implant inserter. Alternatively, the implant or implant inserter can be guided by a flat guide surface 22e or by external features of the shaft 14.

As noted above and referring back to FIG. 1, a filler bar 26 can be removably mated to the distractor 12 to provide rigidity and torque strength to the distractor 12 during insertion into the cavity 42 and distraction of the adjacent vertebrae. As shown in FIG. 1, the filler bar 26 has proximal and distal ends 26a, 26b with a shaft 28 extending therebetween. The proximal end 26a can have a variety of configurations to assist the surgeon with placement and removal of the filler bar 26 from the distractor 12, however as shown the filler bar 26 has a T-shaped handle 30. Alternatively, the proximal end of the filler bar can include a portion of a handle that can mate with a corresponding handle portion on a distractor, such that when mated together, a complete handle is formed. While the handle portions can mate to one another in a variety of ways, in an exemplary embodiment, the handle portions are mated together by a spring lock mechanism.

Extending distally from the T-shaped handle 30 is an elongate shaft 28. While the shaft 28 can have a variety of sizes, as shown it has a diameter that is less than the diameter of the distractor. Additionally, the shaft 28 can have a guide feature 32 that corresponds to the guide feature 18 on the distractor 12. That is, the guide feature 32 can be either protruding or recessed, and have a variety of shapes, such as C-shaped with two opposed sides that can be either straight or curved. While the guide feature 32 can be formed throughout the entire length of the shaft 28 or on a partial length thereof, as shown, the groove 32 is formed throughout the entire length of the shaft 28.

Fixedly attached to the distal most end of the shaft 28 is a stabilizing plate 34. The plate 34 can have any size so long as it is able to fit within the intervertebral space alongside the distractor 12, however in an exemplary embodiment the plate 34 is shaped such that it can nest within the distracting paddle 22, and in particular, within the laterally extending portions of superior and inferior surfaces 22c, 22d. Thus, in an exemplary embodiment, the plate 34 has width that is slightly smaller than the distracting paddle 22 and complementary in shape thereto.

Figure 7:
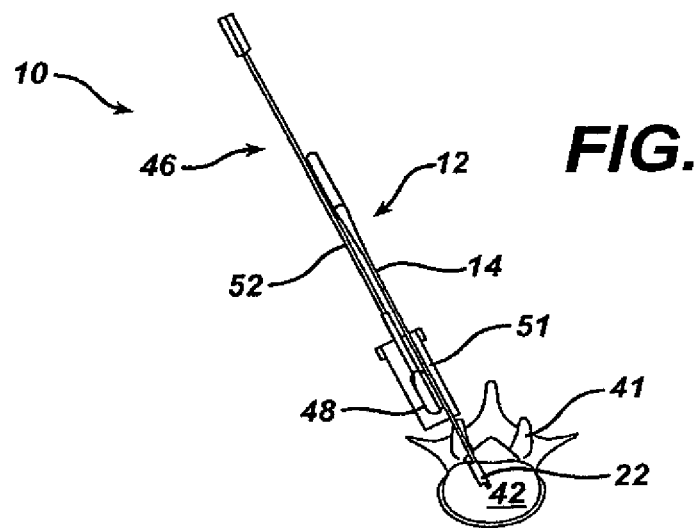
FIG. 7 is a side perspective view of an implant being inserted into an intervertebral space using the distractor assembly of FIG. 1.
Figure 8:
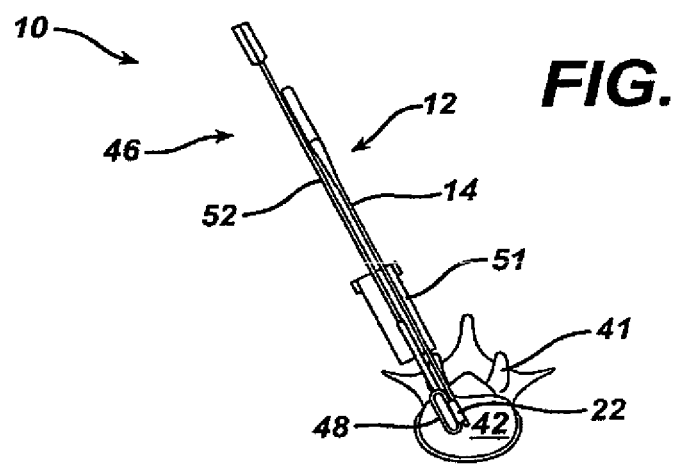
FIG. 8 is another side perspective view of an implant being inserted into an intervertebral space using the distractor assembly of FIG. 1.

In a further embodiment, an implant inserter can be used with the distractor to form a distraction and insertion system. Generally, the inserter can be similar to inserters known in the art, as well as the inserter 46 shown in FIGS. 7 and 8. As shown in FIGS. 7 and 8, the inserter 46 has proximal and distal ends 46a, 46b with a shaft 52 extending therebetween. While the proximal end 46a can have a variety of configurations, in an exemplary embodiment it can have a handle (or a portion thereof) fixedly or removably attached thereto.

Extending distally from the handle of the inserter 46 is an elongate shaft. While the shaft 52 can have a variety of configurations, the shaft 52 can also optionally include a guide feature 50 that corresponds to the guide feature 18 on the distractor 12, such that the inserter 46 can be mated to the distractor 12. Thus, depending upon the configuration of the guide feature 18 on the distractor 12 the guide feature 50 on the inserter 46 can be either protruding or recessed, and can be, for example, C-shaped with two opposed sides that are either straight or curved. Moreover, the guide feature 50 on the inserter 46 can be formed either throughout the entire length of the shaft 52 or on a partial length of the shaft 52. Alternatively, the inserter may simply be guided by a flat surface on the shaft 14 and/or paddle 22 on the distractor 12 or by an external feature of the shaft 14 such as, for example, its superior and/or inferior surfaces. Removably mated to the distal most end of the shaft 52 is an implant 48, various embodiments of which will be discussed below.

In use, as shown in FIGS. 3 to 8, the distraction assembly 10 is inserted into the intervertebral space 42 (that is, the space between superior and inferior vertebrae 41, 43) following the excision of disk material. The distraction assembly 10 is then rotated approximately 90° such that the paddle 22 is substantially perpendicular to the superior and inferior vertebrae 41, 43, so as to enlarge and/or maintain a desired space within the cavity 42 by the force applied to the vertebrae by superior and inferior surfaces 22c, 22d during rotation. One skilled in the art will appreciate that where the instruments are used in a minimally invasive surgical procedure, such as shown in FIGS. 5 to 8, access to the surgical site can be gained using an access port such as cannula 51.

Following distraction of the cavity 42, the filler bar 26 can be removed from the distractor 12 to decrease the amount of space that the assembly 10 requires in order to make room for further tools and/or implants as well as to improve the surgeon's ability to visualize the cavity. As shown in FIGS. 7 to 8, an inserter 46 can then be slidably guided by the distractor 12. Specifically, the surgeon slidably mates the guide features 18, 32, if any, on the distractor 12 and the inserter 46 to one another, and the inserter 46 is slid distally along the distractor 12 into the intervertebral space 42. Once the inserter 46 is placed within the cavity 42, the implant 48 can then be maneuvered so as to achieve the desired orientation.

The distractor assembly disclosed herein can also optionally include a measurement system (not shown). The measurement system can be any indication that allows a surgeon to determine the depth of placement of the distractor, a trial implant or the implant. In an exemplary embodiment, however, the measurement system is formed along the entire length of the shafts of the distractor, filler bar, and/or inserter, or only on a portion thereof. In addition, the distractor can included at least one colored band so as to color code for the height of the distraction paddle that the distractor can be matched to a similarly color coded trial implant and/or implant so that a surgeon can readily ensure that all are of the same height.

As noted above, the distractor assemblies disclosed herein can have a variety of features to assist in implanting the spinal prosthesis, such as those features shown in FIGS. 9 to 43. Specifically, FIGS. 9 to 26 illustrate distractors having features that assist a surgeon in inserting an implant into an intervertebral space at a desired angle. At the outset it should be noted that the distractor of the embodiments described below can have features and methods of use similar to those of distractor 12 discussed above.

Figure 9:
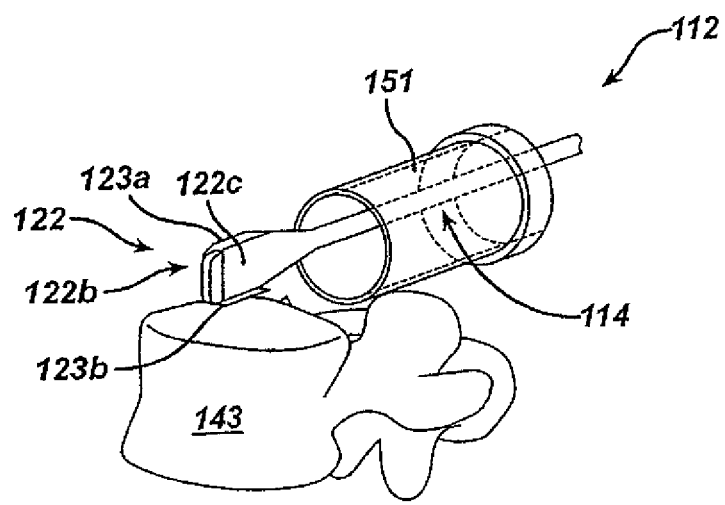
FIG. 9 is a side perspective view of another embodiment of a distractor.
Figure 10:
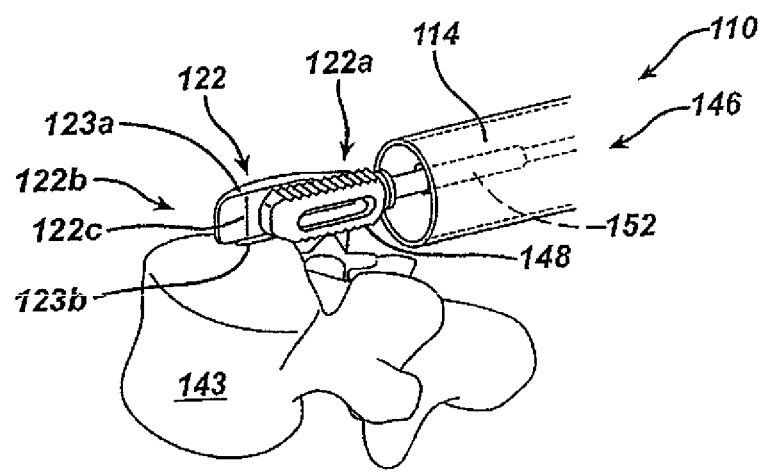
FIG. 10 is a side perspective view of an implant being inserted into an intervertebral space using the distractor of FIG. 9.
Figure 11:
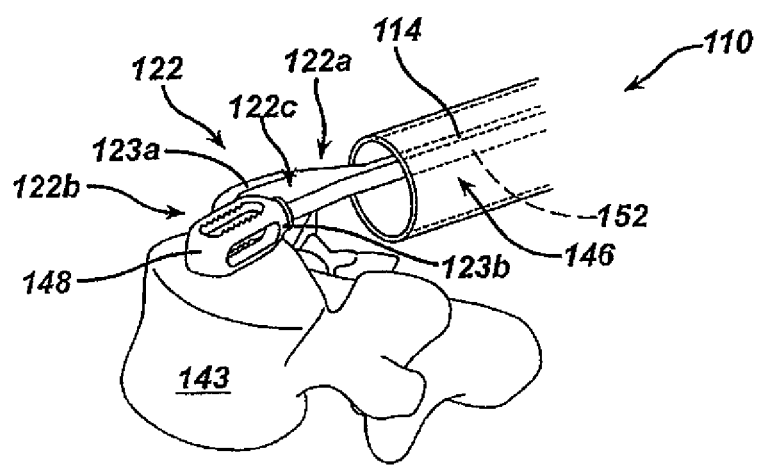
FIG. 11 in another side perspective view of an implant being inserted into an intervertebral space using the distractor of FIG. 9.

FIGS. 9 to 11 illustrate one embodiment of a distractor 112 that includes a paddle 122 having an angled distal end 122b, and thus providing an angled guide surface 122c. Many times, an implant is designed for placement at a certain angle of trajectory between the adjacent vertebrae and/or a surgeon chooses a particular angle of placement in order to achieve desired fusion characteristics. Minimally invasive approaches to the disk space provide well documented advantages, however, establishing a minimally invasive access portal while sparing sensitive nerve tissues from contact and possible damage requires approach angles to the disk space that may not match the desired angle of placement of the implant. For example, a typical TLIF approach may take a 35° angle (plus or minus depending on the anatomy of a particular patient) while the desired angle for placement of the implant may be 45°. Providing an angled distal end 122b on the distractor paddle 122 allows the surgeon to carefully guide the implant during insertion to the desired angle with a reduced chance of contacting sensitive nerve tissue. While the distal end 122b of the paddle 122 can have a variety of angles as desired by the surgeon, in the illustrated embodiment, the distal end 122b of the paddle 122 has an angle of about 20°.

Paddle 122 can further include opposed overhanging tabs 123a, 123b and a curved distal end 122b. The overhanging tabs 123a, 123b can be any configuration that can serve as a guide for the implant 148, however, as shown, the overhanging tabs 123a, 123b are rectangular and extend horizontally from the guide surface 122c of the paddle 122.

In use, as an inserter (such as inserter 146) is slid distally along the shaft 114 of the distractor 112, the overhanging tabs 123a, 123b of the paddle 122 can slidingly engage the outer edge surfaces of the implant 148. Once engaged, the implant 148 is guided along the length of the paddle 122. As the implant 148 approaches the distal end 122b of the paddle 122, the angled distal end 122b urges the implant 148 into the desired orientation within the intervertebral space 142.

Figure 12:
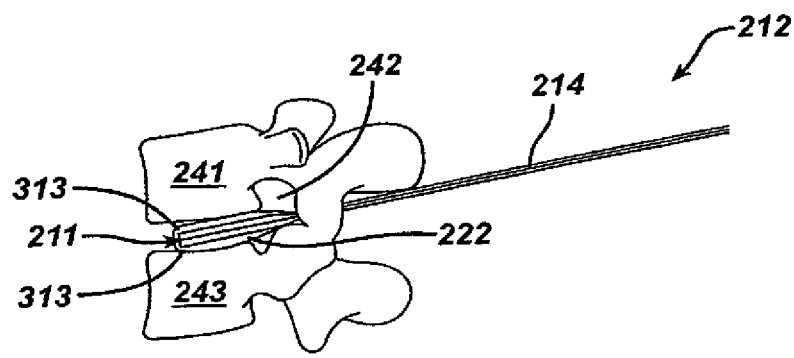
FIG. 12 is a side perspective view of another embodiment of a distractor being inserted into an intervertebral space.
Figure 13:
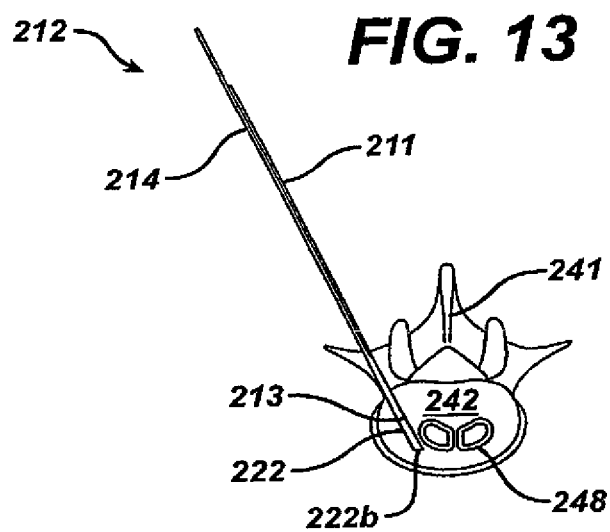
FIG. 13 is a side perspective view of an implant being inserted into an intervertebral space using the distractor of FIG. 12.
Figure 14:
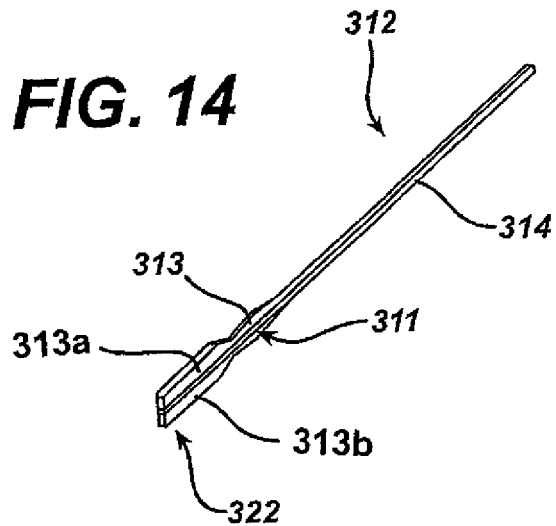
FIG. 14 is a side perspective view of another embodiment of a distractor.
Figure 15:
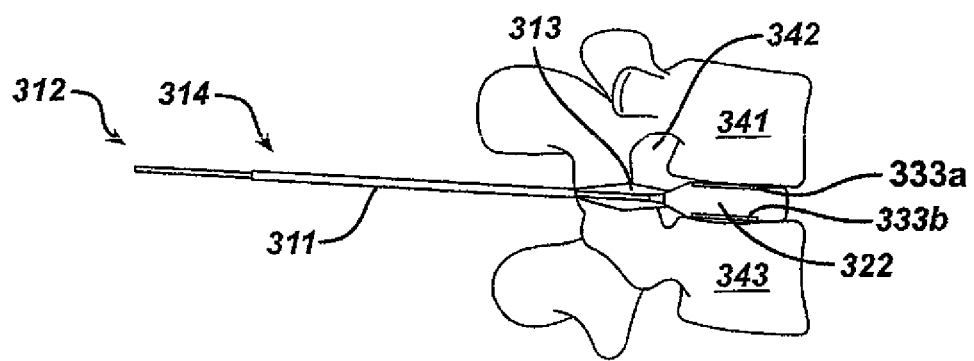
FIG. 15 is a side perspective view of the distractor of FIG. 14 upon insertion into an intervertebral space.
Figure 16:
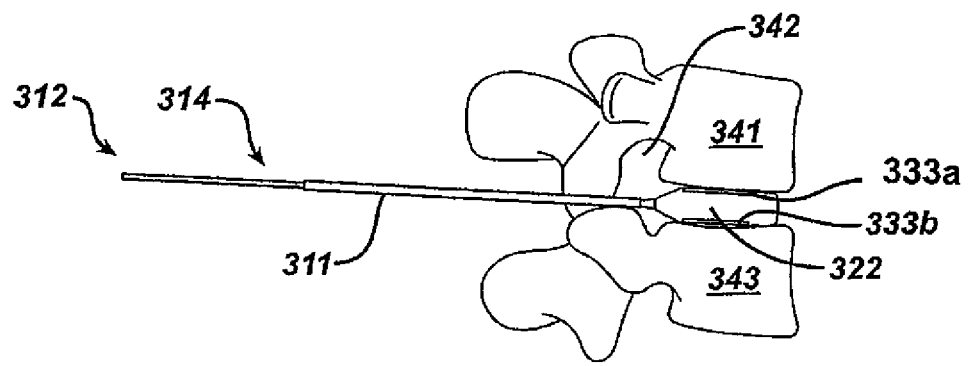
FIG. 16 is another side perspective view of the distractor of FIG. 14 upon insertion into an intervertebral space.
Figure 17:
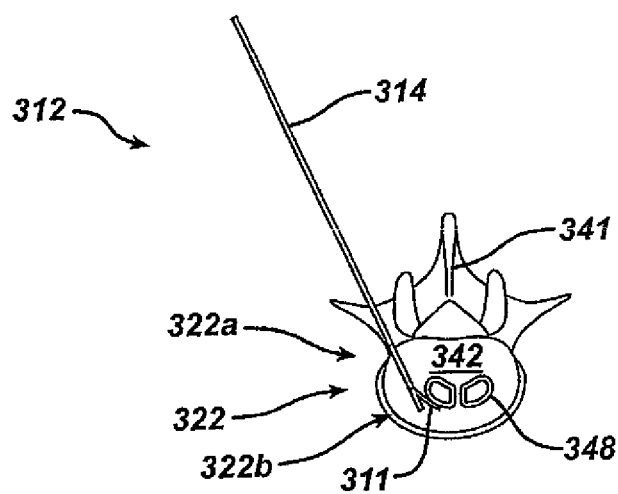
FIG. 17 is a side perspective view of an implant being inserted into an intervertebral space using the distractor assembly of FIG. 14.

FIGS. 12 to 13 illustrate another embodiment of an angled distractor 212 that includes a shape memory metal shim 211. While the metal shim 211 can have any configuration to allow for the angled insertion of an implant 248, as shown the memory metal shim 211 is provided as a separate element from the distractor 212 that is placed along the side of the shaft 214 and paddle 222 of the distractor 212. Shim 211 can be held flat to the shaft 214 and/or paddle 222 of the distractor by one or more guide elements 213.

In use, extension of the shim 211 distally along the paddle 222 (generally by pushing on a proximal end or feature of the shim) beyond the guide elements 213 causes the shim to return to a curved shape. The angle of curvature of the shape memory metal shim 211 can be any angle that allows a surgeon to implant an spinal prosthesis into an intervertebral space 242, however in an exemplary embodiment, the curve of the shim 211 has an angle of about 20°. An implant 248 is then inserted into the intervertebral space 142 and, upon contact with the shim 211, is directed towards the desired placement angle within the intervertebral space 242. The shim 211 can also be retracted/straightened so that retraction of the distractor 212 does not displace the implant and so that retraction of the distractor does not disturb sensitive tissue.

The shim 211 can be made of any biocompatible material known to have shape memory or superelastic properties such as, for example, the NITINOL (an acronym for Nickel Titanium Naval Ordnance Laboratory) family of intermetallic materials, which contain a nearly equal mixture of nickel (55 wt. %) and titanium. One skilled in the art will appreciate that the ability of the shim 211 conform to the shape of the distractor 212 during insertion and then retain its curved shape once it is placed within the intervertebral space 242 allows for a reduced profile for insertion and retraction through a minimally invasive surgical access point.

FIGS. 14 to 17 illustrate an alternate embodiment of a distractor 312 that includes a paddle 322 having a shape memory metal shim 311 similar to metal shim 211 (described above), as well as extension shoulders 333a, 333b. While the extension shoulders 333a, 333b can have a variety of configurations, in an exemplary embodiment, they are slidably located on the paddle 322 and extendable from the superior and inferior sides thereof. However, in an alternate embodiment (not shown), a single extension shoulder can be formed on the paddle.

In use, following insertion into an intervertebral space 342 and rotation of the paddle 322 to a distracting position, the distal movement of the shim 311, and in particular, contact between driving shoulders 313 on the shim 311 and the extension shoulders 333a, 333b, drives the extension shoulders 333a, 333b upward and downward, respectively, to further distract the intervertebral space 342. While extension shoulders 333a, 323b can increase the height of the paddle 322 by any amount as desired by the surgeon to achieve and maintain a desired level of distraction of intervertebral space 342, in an exemplary embodiment, the paddle has a height of approximately 7 mm and extension shoulders 333a, 333b increase the diameter of the paddle 322 by an amount up to approximately 4 mm. By providing at least some of the distraction height by extension rather than rotation, a more sure placement of the distractor can be achieved with less movement within the cavity during distraction. Moreover, following extension of the extension shoulders 333a, 333b, the memory metal shim 311 extends beyond the distal end 322b of the paddle 322, and retains its curved shape, such that the surgeon can place the implant 348 into the cavity 342 at a desired angle.

Figure 18:
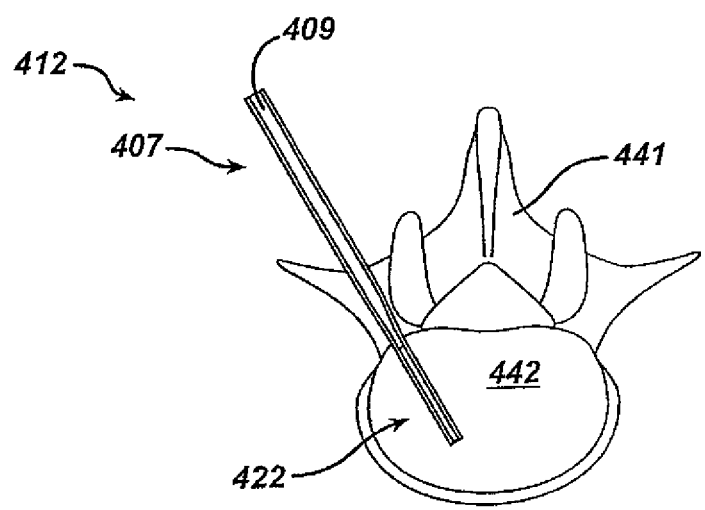
FIG. 18 is a side perspective view of another embodiment of a distractor upon insertion in an intervertebral space.
Figure 19:
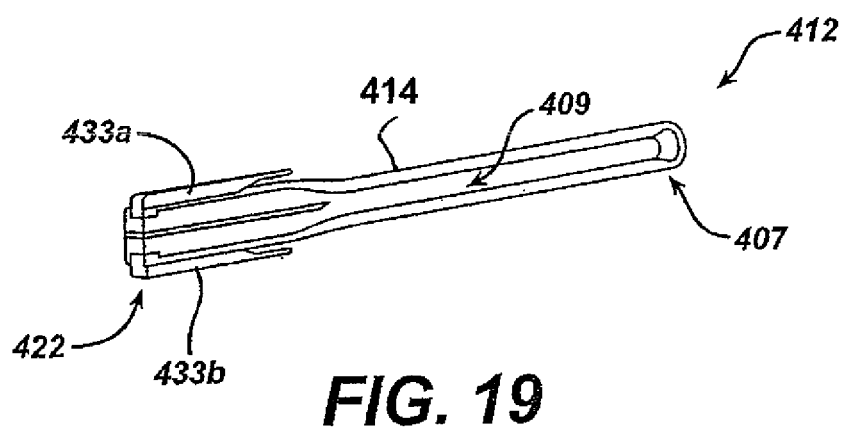
FIG. 19 is a side perspective view of the distractor of FIG. 18.
Figure 20:
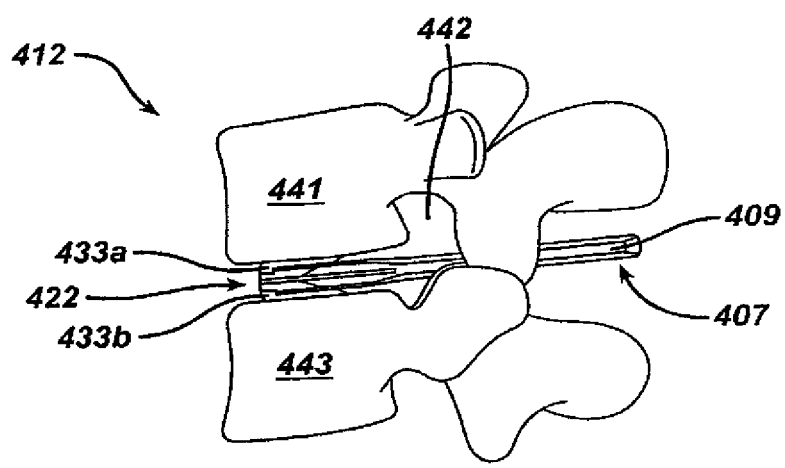
FIG. 20 is another side perspective view of the distractor of FIG. 18 upon insertion into an intervertebral space.

FIGS. 18 to 20 illustrate an alternate embodiment of a distractor 412 having an internal shim 409, as well as extension shoulders 433a, 433b. While the internal shim 409 can be formed in a variety of ways, as shown the internal shim is 409 is formed within a sheath 407 surrounding the shaft 414 of the distractor 412. The internal shim 409 can also include an expansion mechanism such that, in use, and similar to the memory metal shim 211 discussed above, the internal shim 409 drives the extension shoulders 433a, 433b upward and downward, respectively, as the surgeon desires.

Figure 21:
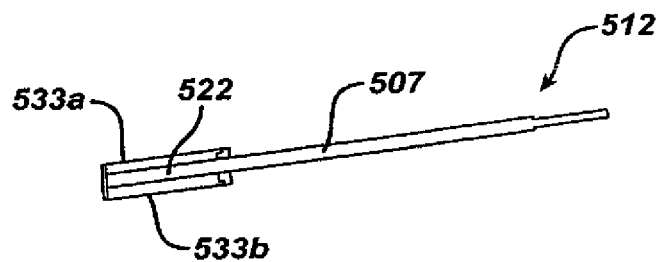
FIG. 21 is a side perspective view of another embodiment of a distractor.
Figure 22:
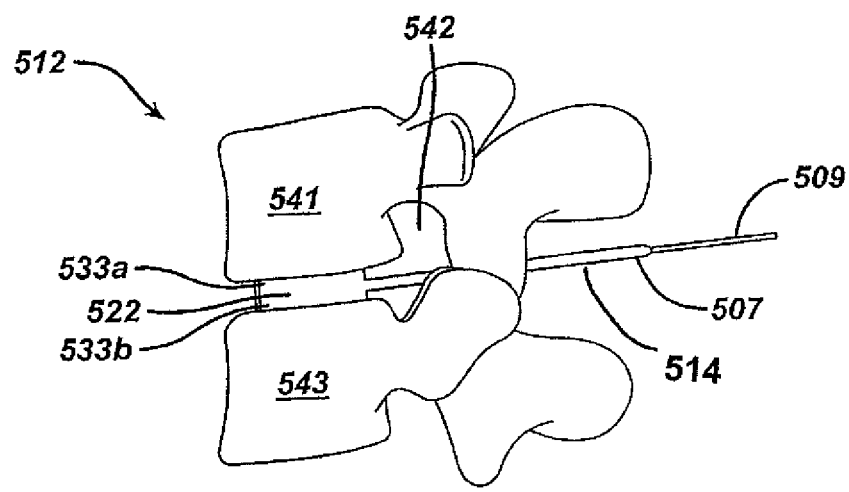
FIG. 22 is a side perspective view of the distractor of FIG. 21 upon insertion into an intervertebral space.
Figure 23:
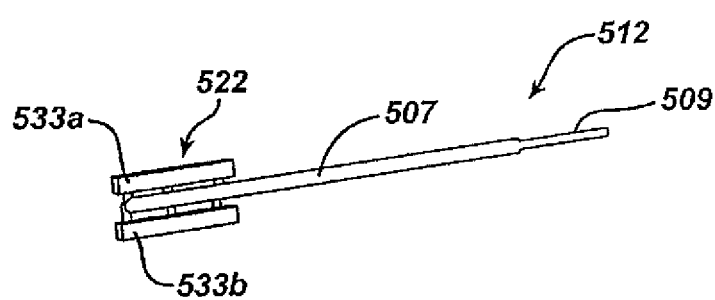
FIG. 23 is another side perspective view of the distractor of FIG. 21.

Alternatively, as shown in FIGS. 21 to 23, the expanding shoulders 533a, 533b of a distractor 512 can be driven by an internal shim 509 having a linkage assembly 505. While the linkage assembly 505 can be formed in a variety of ways, as shown the linkage assembly 505 is also formed within a sheath 507 surrounding the shaft 514 of the distractor 512. In use, similar to the embodiment above, the internal shim 509 can drive the linkage assembly 505 to control the height of the extension shoulders 533a, 533b as desired.

Figure 24:
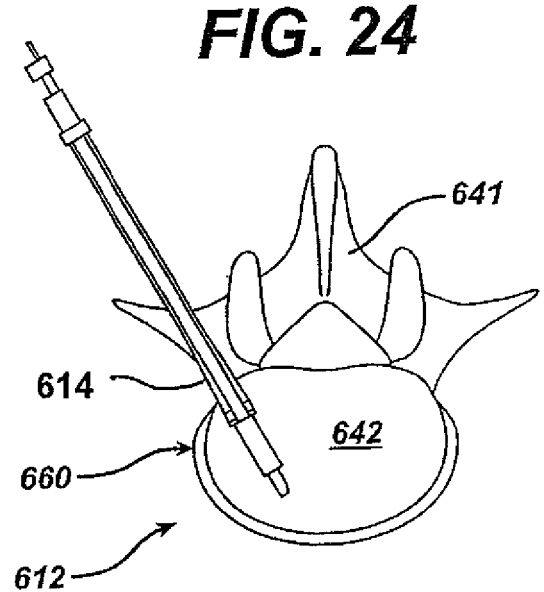
FIG. 24 is a side perspective view of another embodiment of a distractor upon insertion into an intervertebral space.
Figure 25:
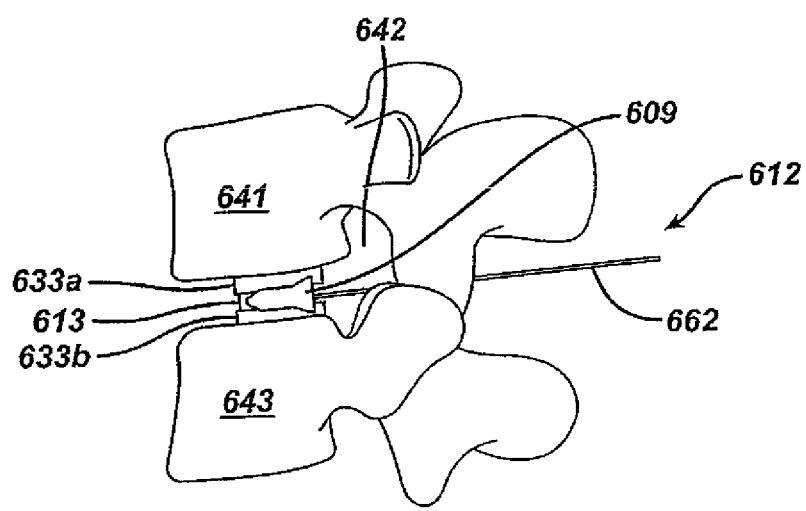
FIG. 25 is another side perspective view of the distractor of FIG. 24 upon insertion into an intervertebral space.
Figure 26:
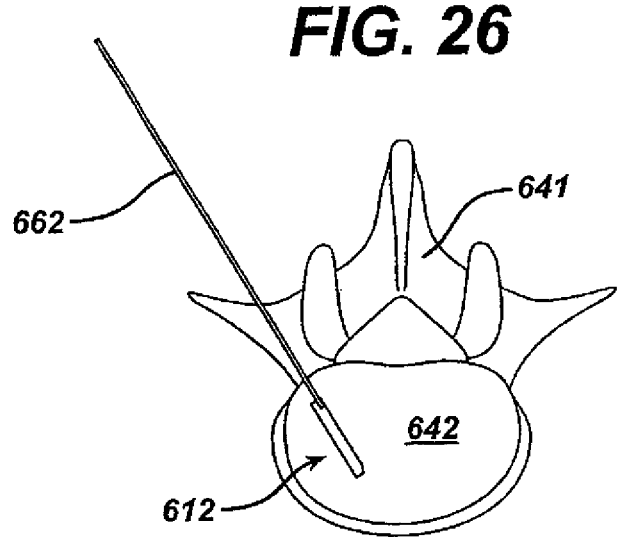
FIG. 26 is another side perspective view of the distractor of FIG. 24 upon insertion into an intervertebral space.

FIGS. 24 to 26 illustrate another embodiment of a distractor 612 having an inserter arm 660 for positioning the distractor. Distractor 612 can include an internal shim 609 and extension shoulders 633a, 633b, similar to those as discussed above. The inserter arm 660 can be removed after placement of the distractor 612, and a cable 662 is left behind extending distally from the distractor 612.

In use, the shim 609 drives the extension shoulders 633a, 633b to set a height adjustment, similar to that as described above with respect to extension shoulders 333a, 333b. Once the cavity 642 is distracted to the desired height, the inserter arm 660 can be slidably removed from the cable 662, resulting in the cable 662 extending out of the intervertebral space 642. The cable 662 can then either be removed or used as a guide for other surgical instruments. One skilled in the art will further appreciate that the shim 609 can also optionally include a sliding support 613 that can be slid along the shaft 614 of the distractor 612 to lock the extension shoulders 633a, 633b in place, and help secure the distracted height of the cavity 642.

The cable 662 can be made from a variety of materials depending upon its desired use by the surgeon. For example, if the surgeon desires the cable to be used as a guide for future instruments or procedures, the cable can be made of any desirable surgical material of sufficient guide strength.

FIGS. 27 to 36 illustrate implant inserters having features that assist a surgeon in inserting an implant into an intervertebral space at a desired angle. At the outset it should be noted that the inserters of the embodiments described below can have features and can be used in a manner similar to that of inserter 46, discussed above. Moreover, depending upon the particular surgical assembly, the shafts of the inserters in the embodiments described below may or may not include a guide feature for slidably engaging with another surgical instrument.

Figure 27:
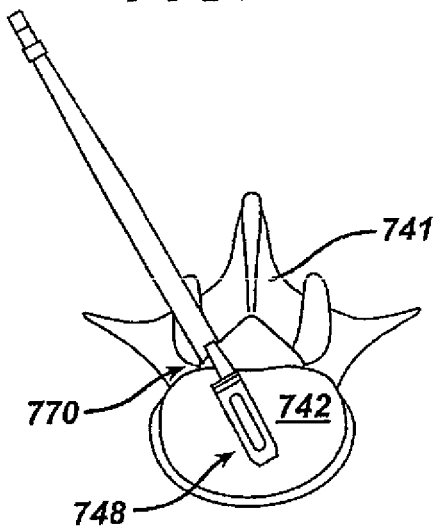
FIG. 27 is a side perspective view of an implant being inserted into an intervertebral space using one embodiment of an inserter.
Figure 28:
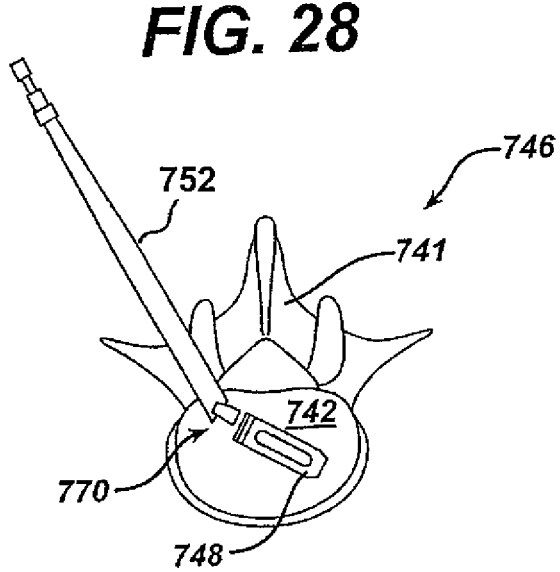
FIG. 28 is another side perspective view of an implant being inserted into an intervertebral space using the inserter of FIG. 27.
Figure 29:
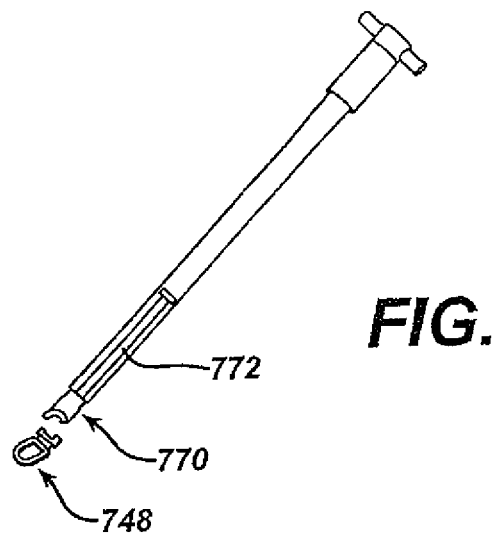
FIG. 29 is a side perspective view of the inserter of FIG. 27.
Figure 30:
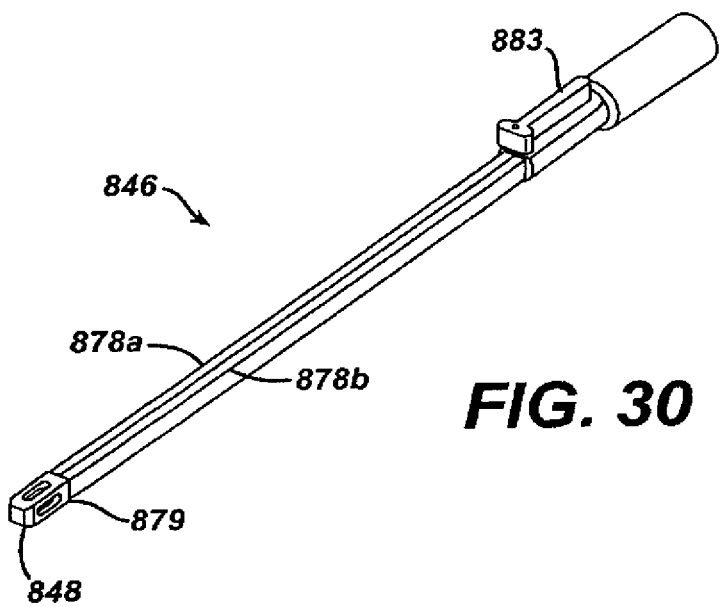
FIG. 30 is a side perspective view of another embodiment of an inserter.
Figure 31:
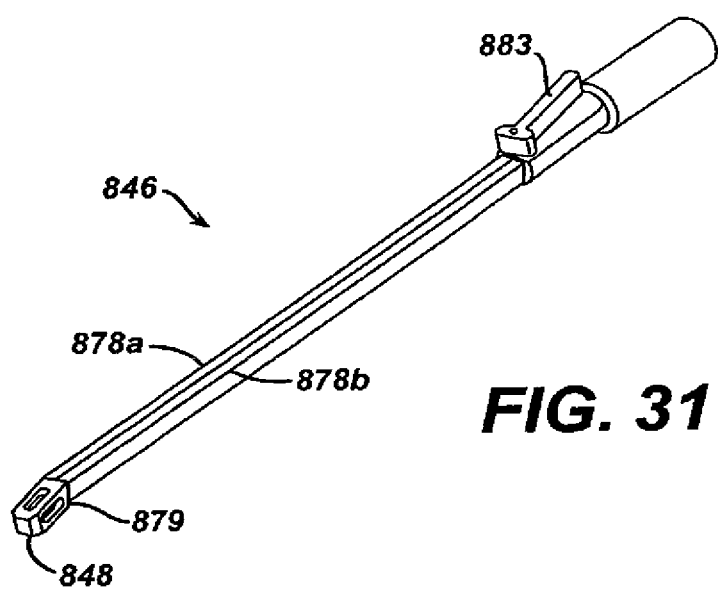
FIG. 31 is another side perspective view of the inserter of FIG. 30.

FIGS. 27 to 29 illustrate one embodiment of an inserter 746 that includes a hinge pivot joint 770 and a linkage mechanism 772. While the hinge pivot joint 770 and the linkage mechanism 772 can have a variety of configurations to drive the implant 748 to desired angulations, in one embodiment, the hinge pivot joint 770 and a linkage mechanism 772 are formed at the distal end 746b of the inserter 746, and located external to the shaft 752 thereof. Alternatively, the hinge pivot joint 770 and the linkage mechanism 772 can be formed within a pathway (not shown) contained within the shaft 752 of the inserter 746. The inserter 746 can also include a variety of means by which the surgeon can control the hinge pivot joint 770 and the linkage assembly 772, such as, for example, a spring bias built into or placed on the pivot joint, and control the movement in response to the bias by proximal or distal movement of the linkage assembly. Thus, in use, the surgeon can maneuver the linkage mechanism such that the hinge pivot joint 770 and a linkage mechanism 772 cooperate to place the implant 748 at a desired angle.

FIGS. 30 to 33 show another embodiment of an inserter 846 that includes mating impaction antis 878a, 878b to rotate the implant 848 to the desired orientation. While the mating impaction arms 878a, 878b can rotate the implant 848 in a variety of ways, as shown, the mating impaction arms 878a, 878b include a mating face 879 that allows high impaction forces on the implant 848 by maintaining a high surface area of contact. Handle or knob 883 is rotated to drive the impaction arms relative to each other so as to rotate the implant, and the position of the knob can indicate the angle to which the implant is rotated as can be seen in the differential angulations illustrated by comparing FIGS. 30 and 31.

Figure 32:
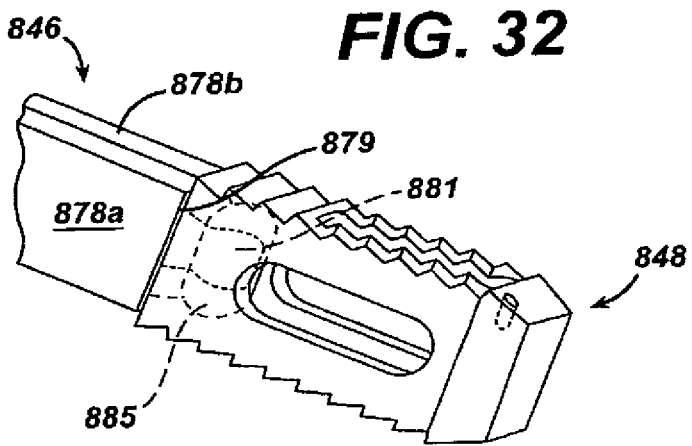
FIG. 32 is a magnified view of the distal end of the inserter of FIG. 30.
Figure 33:
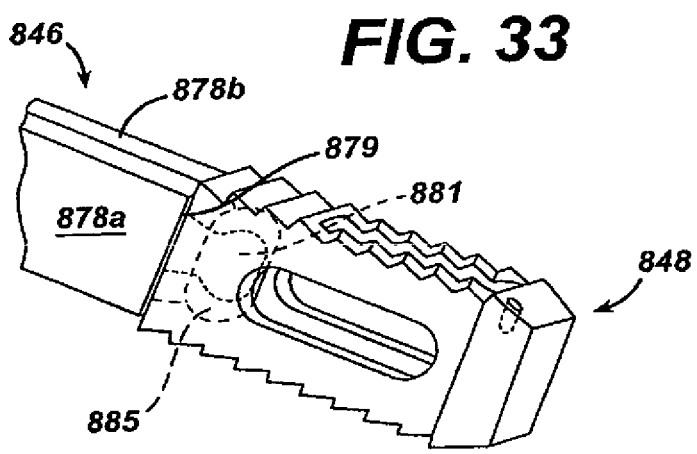
FIG. 33 is another magnified view of the distal end of the inserter of FIG. 30.
Figure 34:
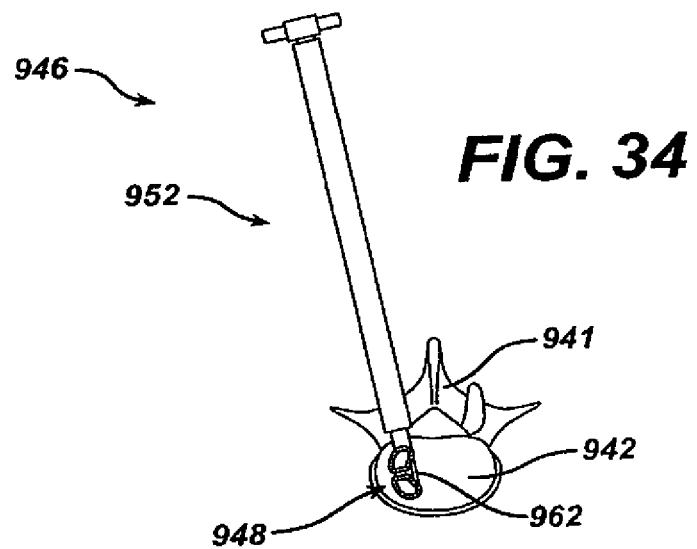
FIG. 34 is a side perspective view of an implant being inserted into an intervertebral space using another embodiment of an inserter.

The mating face 879 can have any configuration, but preferably allows for a high surface area contact with the implant 848, however in an exemplary embodiment the mating face 879 includes an adjustable driving mechanism having a movable protrusion 881 mated to the cavity of an implant 848. FIG. 32 illustrates an up close view of the translating impaction arms described above for an inserter that allows for implant rotation during insertion. The implant 848 includes an internal cavity 885 in which a inserter driver 881 mates while allowing the implant to rotate. The implant 848 is loaded by inserting the driver 881 into the implant cavity 885 and rotating the driver 90 degrees as illustrated in FIG. 34 (loading position) and FIG. 33 (insertion position). The implant 848 can be removed from the inserter by rotating the implant 90 degrees, in the reverse of the loading step for example.

Figure 35:
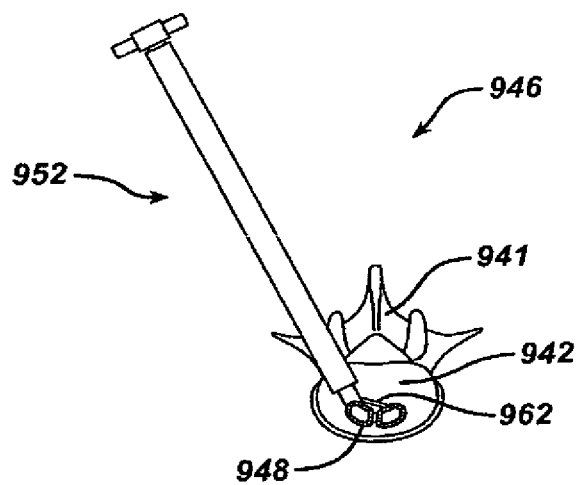
FIG. 35 is another side perspective view of an implant being inserted into an intervertebral space using the inserter of FIG. 34.

FIGS. 34 to 35 illustrates another embodiment of an inserter 946 that allows cable rotation of implant 948 with respect to vertebra 941 by a cable 962 that is linked to the implant 948. Inserter shaft 952 permits rotation of the implant in a hinge-like manner when the cable 962 is operated by the surgeon to drive the rotation. When the inserter shaft 952 is removed, the cable 962 must be disengaged from at least one of the implant 948 (in which case the cable 962 is removed with the shaft 952) or the shaft 952 (in which case the cable 962 is left behind with the implant 948). If the cable 962 is left behind, it can be formed, for example, from a bioabsorbable material.

Figure 36:
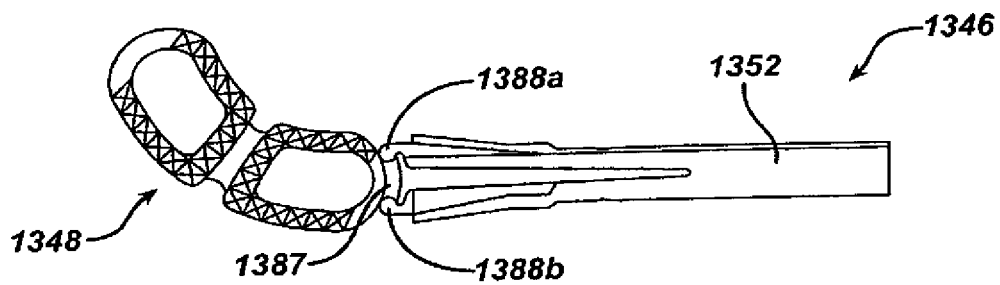
FIG. 36 is a side perspective view of another embodiment of an inserter.

FIG. 36 illustrates an exemplary embodiment of an implant driver 1346 that can be used with inserter 946 to permit rotation of the implant 1348. The implant 1348 includes an external boss feature 1387 that is held between two inserter tabs 1388a, 1388b. The inserter tabs 1388a, 1388b can have a variety of configurations, however in an exemplary embodiment, they include an inserter tab movement mechanism that allows a surgeon to adjust the angulation of the implant 1348, for example by using cable 962 from the embodiment of FIGS. 34 and 35. In one sense, external boss feature 1387 and tabs 1388a, 1388b are the inverse of cavity 885 and inserter driver 881 from the embodiment of FIGS. 32 and 33. Both configurations can allow angulation of the implant, but by contact with external and internal surfaces of the implant respectively.

Figure 37:
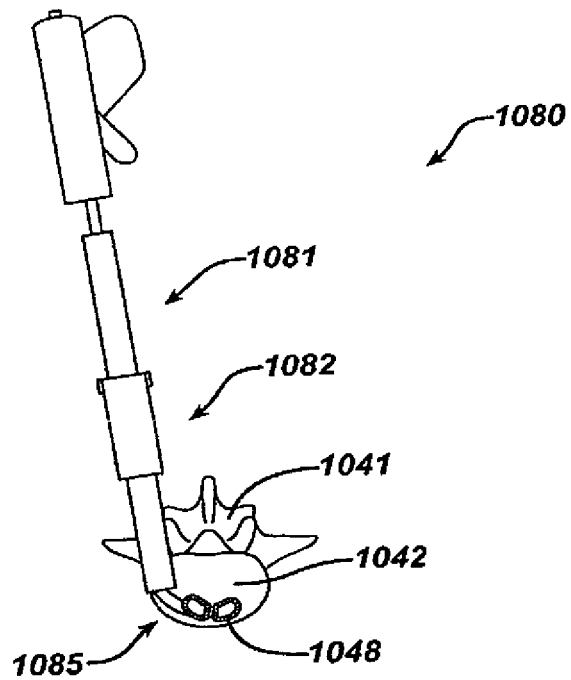
FIG. 37 is a side perspective view of an implant being inserted into an intervertebral space using another embodiment of an inserter.

In other embodiments of the present invention, such as those shown in FIGS. 37-43, the inserter can have a controlled insertion feature to allow incremental insertion and placement of an implant 1048, such as, for example a ratchet gun. Such a gun may have a variety of configurations known in the art, as shown in FIG. 37, the ratchet gun inserter 1080 can include a flexible sheath 1081 to protect the neural tissue from injury during insertion into the intervertebral space 1042 of implant 1048 through minimally invasive access port 1082. Ratchet gun inserter 1080 can further include a flexible inserter connection 1085, such as metal laser cut tubing or helical springs, can be used to allow for implant rotation as described in other embodiments.

Figure 38:
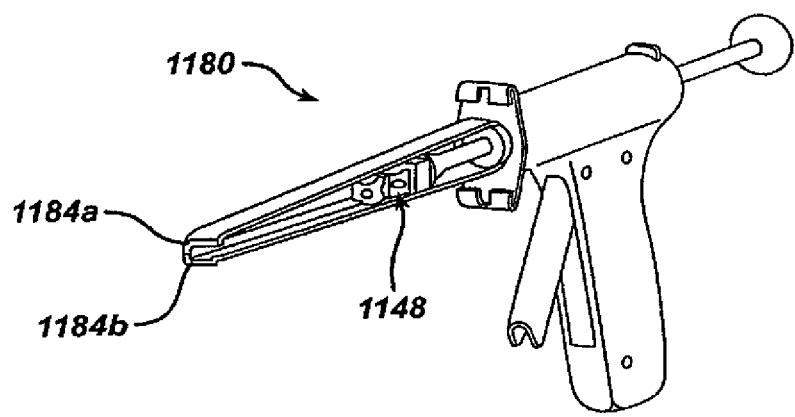
FIG. 38 is a side perspective view of another embodiment of a distractor assembly.
Figure 39:
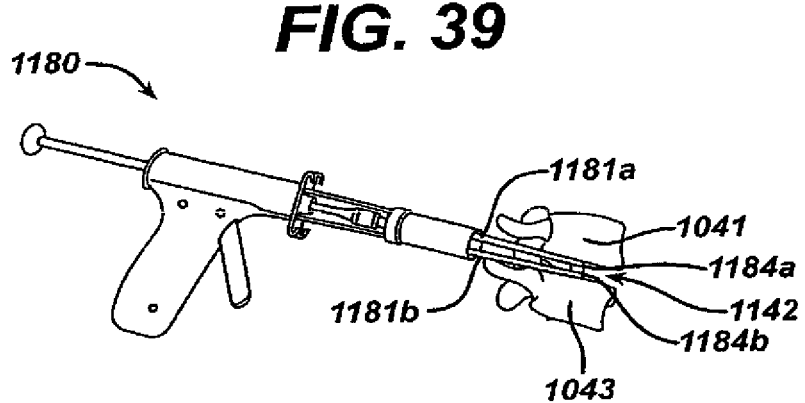
FIG. 39 is a side perspective view of the distractor assembly of FIG. 38 upon insertion into an intervertebral space.

FIGS. 38 and 39 show one embodiment of a ratchet gun 1180 that includes distraction paddles 1184a, 1184b. While the distraction paddles 1184a, 1184b can have a variety of configurations known in the art, in an exemplary embodiment, they extend from the distal most end of the ratchet gun and are shaped and sized such that they fit against the inner surfaces of the superior and inferior vertebrae 1141, 1143. As this embodiment includes paddle distractors, inserter 1180 is not intended to be guided by a paddle distractor as with embodiments described above.

In use, the surgeon inserts the ratchet gun inserter 1180 into the intervertebral space 1142 and squeezes the handle of the gun (likely repeatedly) so that implant 1148 slides between distraction paddles 1184a, 1184b and extends the paddles away from each other to distract the intervertebral space 1142.

Figure 40:
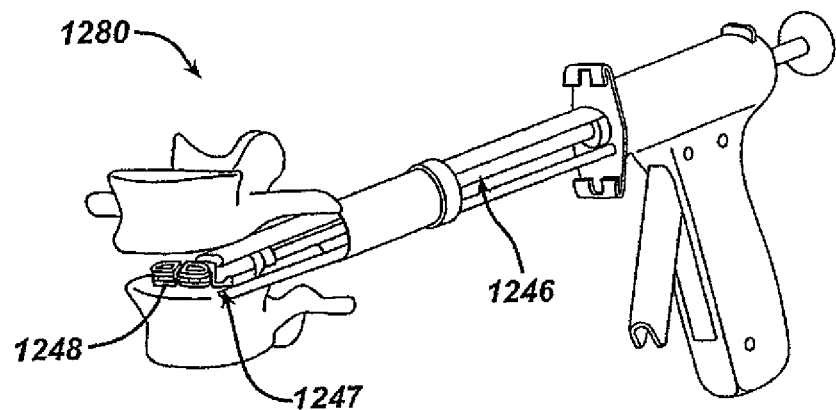
FIG. 40 is a side perspective view of another embodiment of a distractor assembly upon insertion into an intervertebral space.
Figure 41:
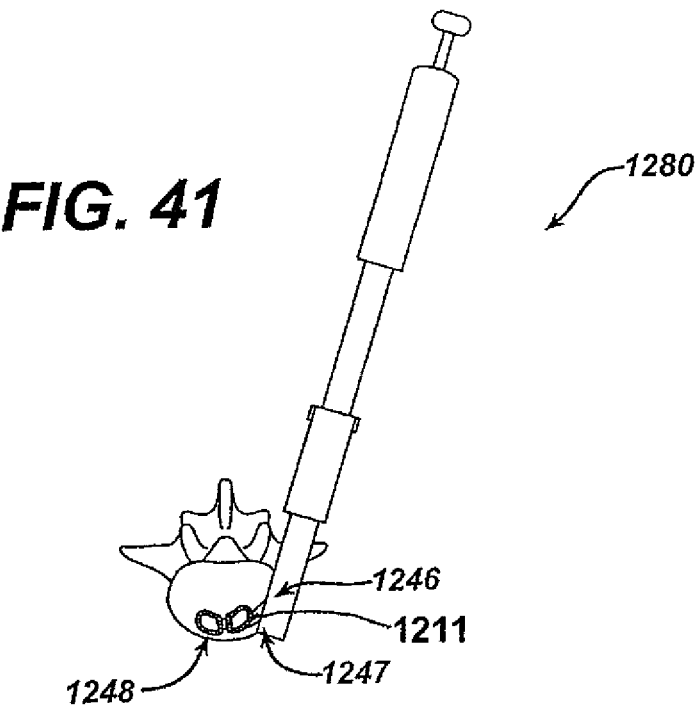
FIG. 41 is another side perspective view of an implant being inserted into an intervertebral space using the distractor assembly of FIG. 40.
Figure 42:
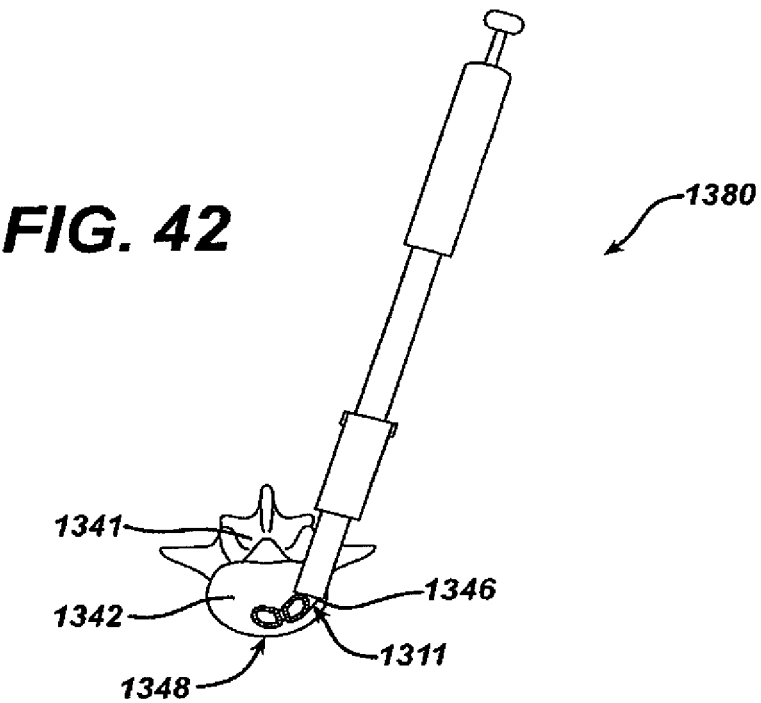
FIG. 42 is a side perspective view of an implant being inserted into an intervertebral space using another embodiment of a distractor assembly.
Figure 43:
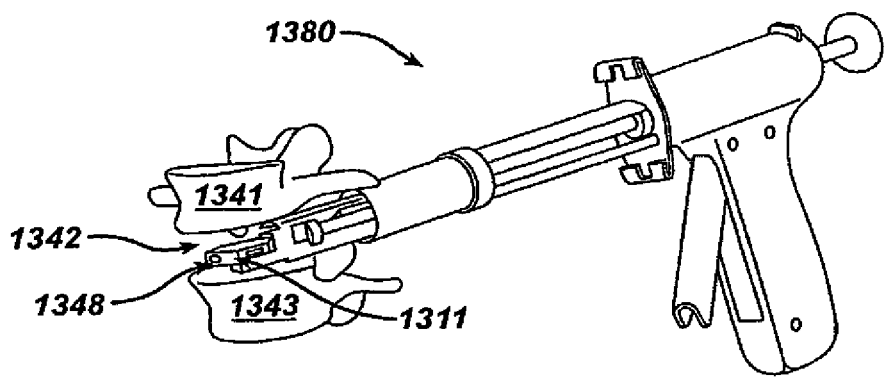
FIG. 43 is another side perspective view of the distractor assembly of FIG. 42 upon insertion into an intervertebral space.

As further shown in FIGS. 40 and 41, a ratchet gun inserter 1280, similar to ratchet gun inserter 1180, can include a rotating inserter 1247 that can have any configuration as described herein (above in FIGS. 27 to 36). Alternatively, as shown in FIGS. 42 and 43, the ratchet gun 1280 can include a memory metal shim 1211, such as that described in FIGS. 12 and 13 above to allow insertion of an implant at a desired angulation.

Figure 44:
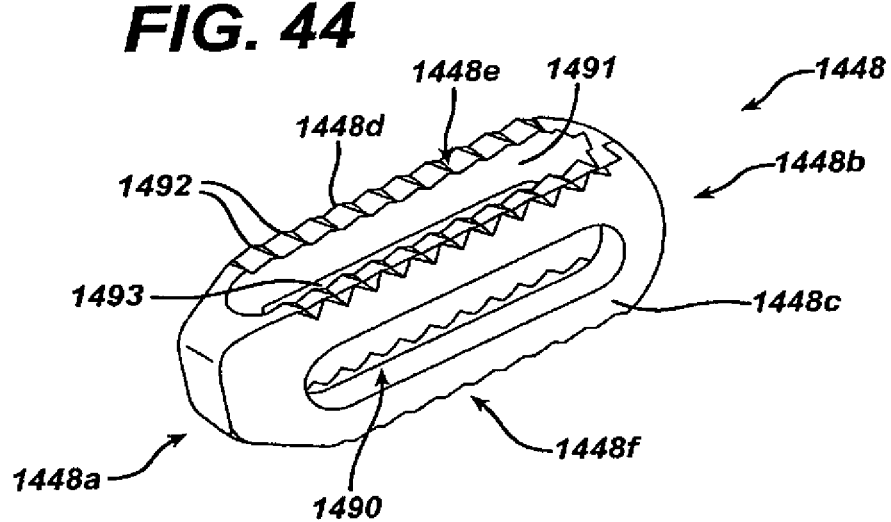
FIG. 44 is a side perspective view of one embodiment of an implant.

A variety of implants can be used with the instruments disclosed above, such as, for example, the implants disclosed in U.S. Pat. No. 4,743,256 to Brantigan, U.S. Pat. No. 4,834,757 to Brantigan, U.S. Pat. No. 4,878,915 to Brantigan, U.S. Pat. No. 5,192,327 to Brantigan, U.S. Pat. No. 5,425,772 to Brantigan, U.S. Pat. No. 5,716,415 to Steffee, U.S. Pat. No. 5,984,922 to Mckay, U.S. Pat. No. 6,245,108 to Biscup, as well as the implants disclosed in FIGS. 44 to 46. While the implants can have a variety of configurations, in an exemplary embodiment, as shown in FIG. 44, the implant 1448 has opposed front and back ends 1448a, 1448b and parallel side surfaces 1448c, 1448d. Upper and lower surfaces 1448e, 1448f that engage the adjacent vertebrae extend between the side surfaces 1448c, 1448d, and such a cavity 1493 is formed within the center of the implant 1448.

The back end 1448b of the implant 1448 can have a profile and features to mate with an inserter instrument such as are known in the art or as described above. Additionally, at least one slot 1490 for vascularization can be formed in at least one of the parallel side surfaces 1448c, 1448d and/or the upper and lower surfaces 1448e, 1448f. While the slots 1490 can have a variety of shapes, e.g., circular, ovular, spherical, as shown the slot is ovular. Additionally, at least one of the parallel side surfaces 1448c, 1448d and/or the upper and lower surfaces 1448e, 1448f has a plurality of pyramid-shaped teeth 1492 formed thereon and extending outward to contact the superior and inferior vertebral surfaces 41, 43 and to resist retropulsion of the implant during or after insertion.

Further, as shown in FIG. 44, the front end 1448a of the implant 1448 can have a geometry that allows for entry into the disk past neural elements and for easier manipulation in the disk space. While this geometry can have a variety of forms, in an exemplary embodiment, it is a bullet-shaped profile, with a bulleted front profile in at least one, but preferably two planes. One skilled in the art will appreciate that the implant having a bullet formed in two planes is able to more effectively distract the vertebrae and neural tissue.

Further, the interior of the parallel side surfaces 1448c, 1448d and/or the upper and lower surfaces 1448e, 1448f can include a plurality of ridges 1491 formed thereon for the maximum retention of the bone graft material within the cavity 1493. While the ridges 1491 can have a variety of shapes, in an exemplary embodiment the ridges 1491 can be slots that extend vertically along the interior surface of the parallel side surfaces 1448c, 1448d and/or the upper and lower surfaces 1448e, 1448f. Alternatively, the ridges 1491 can be slots that horizontally extend along the inner surface of the parallel side surfaces 1448c, 1448d and/or the upper and lower surfaces 1448e, 1448f. Moreover, in an additional embodiment, the inner surfaces of the parallel side surfaces 1448c, 1448d and/or the upper and lower surfaces 1448e, 1448f can include both vertically and horizontally extending ridges 1491.

Figure 45:
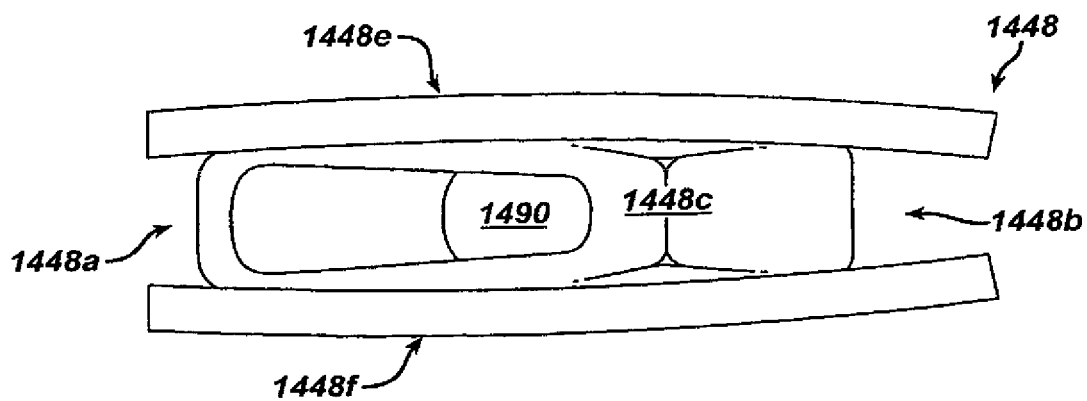
FIG. 45 is a side perspective view of the implant of FIG. 44.
Figure 46:
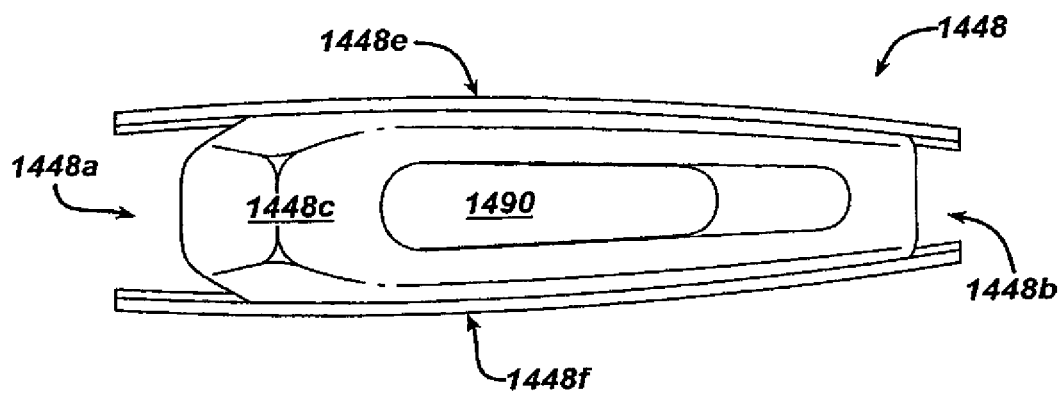
FIG. 46 is another side perspective view of the implant of FIG. 44.

In addition, as shown in FIGS. 45 to 46, upper surface 1448e of the implant 1448 can have a dome structure formed thereon. While the dome can have a variety of configurations, in an exemplary embodiment the dome is angled such that it corresponds to the shape of the superior and inferior vertebrae at a desired angle of rotation. One skilled in the art will appreciate that this implant allows for insertion at an angle that is approximately 35° off of the midline of the vertebrae.

The materials used for forming the implants disclosed herein can vary. One preferred material from which the implant can be made is a carbon fiber reinforced polymer. Other materials from which the implants can be made include metals, metal alloys, biologically compatible polymers, allograft bone, and combinations of these materials. Examples of suitable polymers include polyether sulfone, polycarbonate, and bioabsorbable polymers, and examples of suitable composites include carbon fiber reinforced polymers. Examples of suitable metals include titanium, stainless steel, tantalum, cobalt chromium, aluminum, and combinations thereof.

Figure 47:
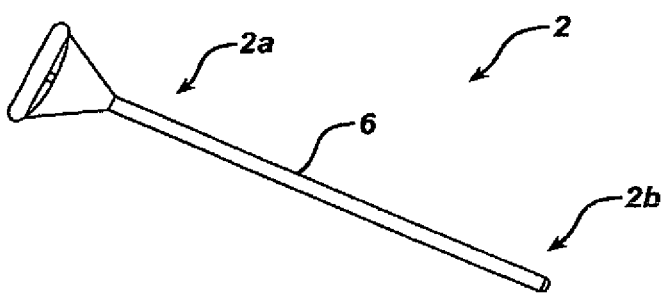
FIG. 47 is a side perspective view of one embodiment of a funnel.

As noted above a graft material funnel 2 can also be used with the distractor assembly disclosed herein. As shown in FIG. 47, the graft material funnel 2 has proximal and distal ends 2a, 2b connected by a shaft 6. The proximal end 2a can have a variety of features known in the art to contain bone graft material to be siphoned into the implant. While the shaft 6 can have a variety of configurations, such as elongate or curved, as shown it is curved. One skilled in the art will appreciate that the curved shape of the shaft allows rotation to implant graft material to a desired location. Additionally, while the shaft 6 can be made from a variety of materials, in an exemplary embodiment, the shaft 6 is made from a material that allows for the shaft diameter to have some flexibility, such that the graft material can be introduced into the funnel 2 without clogging.

The instruments described herein can be made from any suitable surgical grade material, including surgical grade stainless steel, titanium, aluminum, tantalum, cobalt chromium, plastics, and combinations and copolymers thereof.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical instrument system, comprising:
   an articulating implant inserter including
     a shaft; and
     an articulatable implant holding element having a hinge pivot joint and located on a distal end of the shaft, the articulatable implant holding element being operable from a proximal portion of the shaft to releasably hold an implant; and
   an implant having a connecting element that cooperates with the articulatable implant holding element to allow articulation of the implant to a desired angle upon operation of the implant holding element.

2. The system of claim 1, wherein the implant connecting element is internal to the implant.

3. The system of claim 1, wherein the implant connecting element is external to the implant.

4. The system of claim 1, wherein the articulatable implant holding element includes two sliding elements having distal implant impaction faces, the implant holding element being operable from a proximal handle to provide relative sliding in a proximal-distal direction along the shaft to selectively articulate the implant to a desired angle.

5. The system of claim 4, wherein the position of the handle acts as a visual indicator for an angle through which the implant has been rotated.

6. The system of claim 1, wherein the implant is a fusion cage.

7. A surgical instrument system, comprising:
   an articulating implant inserter including
     a shaft; and
     an articulatable implant holding element located on a distal end of the shaft, the articulatable implant holding element being operable from a proximal portion of the shaft to releasably hold an implant; and
   an implant having a connecting element that cooperates with the articulatable implant holding element to allow articulation of the implant to a desired angle upon operation of the implant holding element;
   wherein the articulatable implant holding element includes two sliding elements having distal implant impaction faces, the implant holding element being operable from a proximal handle to provide relative sliding in a proximal-distal direction along the shaft to selectively articulate the implant to a desired angle; and
   wherein the position of the handle acts as a visual indicator for an angle through which the implant has been rotated.

8. The system of claim 1, wherein the implant connecting element is internal to the implant.

9. The system of claim 7, wherein the implant is a fusion cage.

* * * * *